(12) United States Patent
Valdastri et al.

(10) Patent No.: US 11,122,965 B2
(45) Date of Patent: Sep. 21, 2021

(54) ROBOTIC CAPSULE SYSTEM WITH MAGNETIC ACTUATION AND LOCALIZATION

(71) Applicant: Vanderbilt University, Nashville, TN (US)

(72) Inventors: Pietro Valdastri, Leeds (GB); Piotr R. Slawinski, Lincoln, NE (US); Addisu Z. Taddese, Nashville, TN (US); Keith L. Obstein, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 406 days.

(21) Appl. No.: 16/155,637

(22) Filed: Oct. 9, 2018

(65) Prior Publication Data
US 2019/0104994 A1    Apr. 11, 2019

Related U.S. Application Data

(60) Provisional application No. 62/569,990, filed on Oct. 9, 2017.

(51) Int. Cl.
*A61B 1/00*    (2006.01)
*A61B 5/00*    (2006.01)
(Continued)

(52) U.S. Cl.
CPC ........ *A61B 1/00158* (2013.01); *A61B 1/0008* (2013.01); *A61B 1/00149* (2013.01);
(Continued)

(58) Field of Classification Search
CPC ............ A61B 34/20; A61B 2034/2046; A61B 2034/2051; A61B 2034/2053;
(Continued)

(56) References Cited

U.S. PATENT DOCUMENTS 3,315,660 A    4/1967 Abella
3,858,572 A    1/1975 Binard et al.
(Continued)

FOREIGN PATENT DOCUMENTS

CN    101778592 A    7/2010
DE    102006019419 A1    11/2007
(Continued)

OTHER PUBLICATIONS

Valdastri et al., "Magnetic air capsulerobotic system: Proof of concept of a novel approach for painless colonoscopy," Surgical Endoscopy, 2011, in press, 1 page.
(Continued)

*Primary Examiner* — Ryan N Henderson
*Assistant Examiner* — Amir Jamal Al Khatib
(74) *Attorney, Agent, or Firm* — Michael Best & Friedrich LLP

(57) ABSTRACT

Systems and methods are presented for localization of a capsule based on magnetic fields. The capsule is positioned in a magnetic field generated by a first magnet and an electromagnetic coil is operated to generate a sinusoidal magnetic field with a magnetic moment orthogonal to the magnetic moment of the first magnet. An average signal measurement calculated for each magnetic field sensor is defined as the magnetic field applied to the magnetic field sensor by the first magnet and used as an offset to determine the magnetic field applied by the electromagnetic coil. The pose of the capsule is then determined based at least in part on a combination of magnetic field signals applied by the electromagnetic coil to each of the magnetic field sensors.

6 Claims, 11 Drawing Sheets

(51) Int. Cl.
*A61B 1/04* (2006.01)
*A61B 5/06* (2006.01)
*A61B 34/00* (2016.01)
*A61B 34/20* (2016.01)
*A61B 1/018* (2006.01)

(52) U.S. Cl.
CPC .............. *A61B 1/018* (2013.01); *A61B 1/041* (2013.01); *A61B 5/062* (2013.01); *A61B 5/6861* (2013.01); *A61B 34/73* (2016.02); *A61B 2034/2048* (2016.02); *A61B 2034/2051* (2016.02); *A61B 2034/731* (2016.02)

(58) Field of Classification Search
CPC ............ A61B 1/00147; A61B 1/00149; A61B 1/00158; A61B 1/041; A61B 2034/731–733; A61B 5/6861; A61B 5/062; A61B 1/0008; A61B 1/018; A61B 2034/2048; A61B 2560/00; A61B 2562/162; A61B 1/00; A61B 1/04
See application file for complete search history.

(56) References Cited

U.S. PATENT DOCUMENTS

| | | | |
|---|---|---|---|
| 3,870,072 | A | 3/1975 | Lindemann |
| 4,048,992 | A | 9/1977 | Lindemann et al. |
| 4,207,887 | A | 6/1980 | Hiltebrandt et al. |
| 4,287,809 | A | 9/1981 | Egli et al. |
| 4,314,251 | A | 2/1982 | Raab |
| 4,769,006 | A | 9/1988 | Papantonakos |
| 4,991,957 | A | 2/1991 | Sakamoto et al. |
| 5,330,486 | A | 7/1994 | Wilk |
| 5,489,256 | A | 2/1996 | Adair |
| 6,248,080 | B1 | 6/2001 | Miesel et al. |
| 6,270,787 | B1 | 8/2001 | Ayer |
| 6,802,811 | B1 | 10/2004 | Slepian |
| 7,722,559 | B2 | 5/2010 | Uesugi et al. |
| 7,647,090 | B1 | 11/2010 | Frisch et al. |
| 8,652,102 | B2 | 2/2014 | Nitsan et al. |
| 2001/0051766 | A1 | 12/2001 | Gazdzinski |
| 2002/0065455 | A1 | 5/2002 | Ben-Haim et al. |
| 2003/0114731 | A1 | 6/2003 | Cadeddu et al. |
| 2003/0214579 | A1 | 11/2003 | Iddan |
| 2003/0214580 | A1 | 11/2003 | Iddan |
| 2005/0124928 | A1 | 6/2005 | Beck |
| 2005/0154277 | A1 | 7/2005 | Tang et al. |
| 2005/0267334 | A1 | 12/2005 | Swain et al. |
| 2005/0277852 | A1 | 12/2005 | Shih et al. |
| 2006/0004276 | A1 | 1/2006 | Iddan et al. |
| 2006/0188407 | A1 | 8/2006 | Gable et al. |
| 2007/0015968 | A1 | 1/2007 | Shelnutt |
| 2007/0221233 | A1 | 9/2007 | Kawano |
| 2008/0015413 | A1 | 1/2008 | Barlow et al. |
| 2008/0021334 | A1 | 1/2008 | Finburgh et al. |
| 2008/0058835 | A1 | 3/2008 | Farritor et al. |
| 2008/0154093 | A1 | 6/2008 | Cho et al. |
| 2008/0207999 | A1 | 8/2008 | Abraham-Fuchs et al. |
| 2008/0300453 | A1 | 12/2008 | Aoki et al. |
| 2008/0300458 | A1 | 12/2008 | Kim et al. |
| 2009/0024142 | A1 | 1/2009 | Ruiz Morales |
| 2009/0054877 | A1 | 2/2009 | Hood et al. |
| 2009/0054909 | A1 | 2/2009 | Farritor |
| 2009/0171268 | A1 | 7/2009 | Williams, Jr. et al. |
| 2009/0171373 | A1 | 7/2009 | Farritor et al. |
| 2009/0182197 | A1 | 7/2009 | Goldwasser et al. |
| 2009/0292205 | A1 | 11/2009 | Osaka |
| 2010/0049120 | A1 | 2/2010 | Dijksman et al. |
| 2010/0100117 | A1 | 4/2010 | Brister et al. |
| 2010/0198008 | A1 | 8/2010 | Kawano |
| 2010/0256636 | A1 | 10/2010 | Fernandez et al. |
| 2011/0184235 | A1 | 7/2011 | Schostek et al. |
| 2011/0202070 | A1 | 8/2011 | Dario et al. |
| 2011/0301497 | A1 | 12/2011 | Shachar et al. |
| 2011/0313415 | A1 | 12/2011 | Fernandez et al. |
| 2012/0035416 | A1 | 2/2012 | Fernandez et al. |
| 2012/0041345 | A1 | 2/2012 | Rajamani et al. |
| 2012/0149981 | A1* | 6/2012 | Khait ................. A61B 1/00158 600/109 |
| 2012/0232362 | A1 | 9/2012 | Gable et al. |
| 2012/0238796 | A1 | 9/2012 | Conlon |
| 2012/0271555 | A1 | 10/2012 | Levental et al. |
| 2013/0018224 | A1 | 1/2013 | Kim et al. |
| 2013/0131695 | A1 | 5/2013 | Scarfogliero et al. |
| 2013/0165859 | A1 | 6/2013 | Imran |
| 2013/0225922 | A1 | 8/2013 | Schentag et al. |
| 2013/0245356 | A1 | 9/2013 | Fernandez et al. |
| 2013/0298715 | A1 | 11/2013 | Valdastri et al. |
| 2013/0324914 | A1 | 12/2013 | Valdastri et al. |
| 2014/0081120 | A1 | 3/2014 | Valdastri et al. |
| 2014/0081169 | A1 | 3/2014 | Gerding et al. |
| 2014/0206953 | A1 | 7/2014 | Valdastri et al. |
| 2014/0206956 | A1 | 7/2014 | Rabinovitz et al. |
| 2014/0249372 | A1 | 9/2014 | Yoshida et al. |
| 2014/0276941 | A1* | 9/2014 | Rodriguez-Navarro ..................... A61B 17/0281 606/130 |
| 2014/0358162 | A1 | 12/2014 | Valdastri et al. |
| 2015/0018614 | A1* | 1/2015 | Duan ..................... A61B 34/73 600/109 |
| 2015/0045725 | A1 | 2/2015 | Smith et al. |
| 2015/0342501 | A1 | 12/2015 | Di Natali et al. |
| 2016/0100771 | A1* | 4/2016 | Chiba .................... A61B 5/062 600/424 |
| 2017/0245741 | A1 | 8/2017 | Valdastri et al. |

FOREIGN PATENT DOCUMENTS

| | | |
|---|---|---|
| EP | 2286756 A1 | 2/2011 |
| EP | 2163206 B1 | 12/2012 |
| JP | H104144533 | 5/1992 |
| WO | 9405200 | 3/1994 |
| WO | 2000030548 A1 | 6/2000 |
| WO | 2004041068 A2 | 5/2004 |
| WO | 2006045011 A2 | 4/2006 |
| WO | 2007013059 A2 | 2/2007 |
| WO | 2007146987 A2 | 12/2007 |
| WO | 2008016196 | 2/2008 |
| WO | 2008122997 A1 | 10/2008 |
| WO | 2009014917 A2 | 1/2009 |
| WO | 2010042611 A1 | 4/2010 |
| WO | 2010044053 A2 | 4/2010 |
| WO | 2010046823 A1 | 4/2010 |
| WO | 2011058505 A1 | 5/2011 |
| WO | 2011135503 A1 | 11/2011 |
| WO | 2012028557 A1 | 3/2012 |
| WO | 2012035157 A1 | 3/2012 |
| WO | 2012080947 A1 | 6/2012 |
| WO | 2012164517 A1 | 12/2012 |
| WO | 2013027182 A1 | 2/2013 |

OTHER PUBLICATIONS

Valdastri et al., "Micromanipulation, Communication and Swarm Intelligence Issues in a Swarm Microrobotic Platform", Robotics and Autonomous Systems, 2006, vol. 54, No. 10, pp. 789-804.
Valdastri et al., "Miniaturised Cutting Tool with Triaxial Force Sensing Capabilities for Minimally Invasive Surgery", ASME Journal of Medical Devices, 2007, vol. 1, N. 3, pp. 206-211.
Valdastri et al., "Transmission Power Requirements for Novel ZigBee Implants in the Gastrointestinal Tract", IEEE Transactions on Biomedical Engineering, 2008, vol. 55, No. 6, pp. 1705-1710.
Valdastri et al., "Wireless implantable electronic platform for chronic fluorescent-based biosensors", IEEE Transactions on Biomedical Engineering, 2011, vol. 58, No. 6, pp. 1846-1854.
Valdastri et al., "Wireless Therapeutic Endoscopic Capsule: in-vivo Experiment", Endoscopy, 2008, vol. 40, pp. 979-982.
Van Der Meijden et al., "The value of haptic feedback in conventional and robot-assisted minimal invasive surgery and virtual reality training: a current review," Surgical Endoscopy, vol. 23, pp. 1180-1190, 2009.

(56) References Cited

OTHER PUBLICATIONS

Van Gossum et al., Capsule endoscopy versus colonoscopy for the detection of polyps and cancer. N Engl J Med, 361(3):264-270, Jul. 2009.
Varadarajulu et al., "GI Endoscopes," Gastrointestinal Endoscopy, vol. 74, No. 1, pp. 1-6.e6, Jul. 2011.
Vatteroni et al., "Linear-logarithmic CMOS pixel with tunable dynamic range", IEEE Transactions on Electron Devices, 2011, vol. 58, No. 4, pp. 1108-1115.
Vatteroni et al., "Smart optical CMOS sensor for endoluminal applications", Sensors and Actuators A: Physical, 2010, vol. 162, No. 2, pp. 297-303.
Vucelic et al., The Aer-o-Scope: proof of concept of a pneumatic, skill-independent, self-propelling, self-navigating colonoscope. Gastroenterology, 130:672-677, 2006.
Wang et al., "Novel Medical Wired Palpation Device: A Device Validation Study of Material Properties", Transducers 2013, Barcelona, Spain, pp. 1653-1658.
Webster et al., "Design and Kinematic Modeling of Constant Curvature Continuum Robots: A Review," The International Journal of Robotics Research, vol. 29, No. 13, pp. 1661-1683, Jun. 2010.
Webster et al., "Mechanics of Precurved-Tube Continuum Robots," IEEE Transactions on Robotics, vol. 25, No. 1, pp. 67-78, Feb. 2009.
Wellman et al., "Extracting Features from Tactile Maps," Proceedings of the Second International Conference on Medical Image Computing and Computer-Assisted Intervention, vol. 167, pp. 1133-1142, 1999.
Wellman et al., "Tactile Imaging of Breast Masses: First Clinical Report," vol. 136, No. 2, pp. 204-248, 2001.
Wellman et al., "Tactile imaging: a method for documenting breast lumps," 1999, vol. 2, p. 1131.
White et al., "Surgical Technique: Static Intramedullary Nailing of the Femur and Tibia Without Intraoperative Fluoroscopy.," Clinical orthopaedics and related research, pp. 3469-3476, Mar. 2011.
Wilhelm et al., "Gastrointestinal Endoscopy in a Low Budget Context: Delegating EGD to Non-Physician Clinicians in Malawi can be Feasible and Safe." Endoscopy, vol. 44, No. 2, pp. 174-176, Feb. 2012.
Wilkins et al., The current state of flexible sigmoidoscopy training in family medicine residency programs. Family Medicine, 37:706-11, 2005.
Wilkins et al., "Colorectal cancer: A summary of the evidence for screening and prevention," Am Fam Physician. Dec. 15, 2008;78(12):1385-1392.
Wong et al., Towards painless colonoscopy: A randomized controlled trial on carbon dioxide-insufflatingcolonoscopy. ANZ Journal of Surgery, 78 (10):871-874, 2008.
Xu et al., "Actuation Compensation for Flexible Surgical Snake-like Robots with Redundant Remote Actuation," in IEEE International Conference on Robotics and Automation, 2006, pp. 4148-4154.
Xu et al., "An Investigation of the Intrinsic Force Sensing Capabilities of Continuum Robots," IEEE Transactions on Robotics, vol. 24, No. 3, pp. 576-587, 2008.
Xu et al., "Analytic Formulation for Kinematics, Statics and Shape Restoration of Multibackbone Continuum Robots via Elliptic Integrals," ASME Journal of Mechanisms and Robotics (JMR), vol. 2, pp. 11006-11013, 2010.
Xu et al., "Intrinsic Wrench Estimation and Its Performance Index for Multisegment Continuum Robots," IEEE Transactions on Robotics, vol. 26, No. 3, pp. 555-561, Jun. 2010.
Xu, "Design, Modeling and Analysis of Continuum Robots as Surgical Assistants with Intrinsic Sensory Capabilities," Ph.D. Dissertation, (Advisor: N. Simaan), Mechanical Engineering, Columbia University, 2009, 1-24.
Yamamoto et al., "Techniques for Environment Parameter Estimation During Telemanipulation," pp. 217-223, 2008.
Yim et al., "Biopsy Using a Magnetic Capsule Endoscope Carrying, Releasing, and Retrieving Untethered . Microgrippers." IEEE Trans. Biomed. Eng., vol. 61, No. 2, pp. 513-21, Feb. 2014.

Yim et al., "Design and Analysis of a Magnetically Actuated and Compliant Capsule Endoscopic Robot," 2011 IEEE Int. Conf. Robot. Autom., pp. 4810-4815, May 2011.
Yim et al., "Magnetically Actuated Soft Capsule With the Multimodal Drug Release Function," IEEE/ASME Trans. Mechatronics, vol. 18, No. 4, pp. 1413-1418, 2013.
Zbyszewskli et al., "Air-cushion force sensitive probe for soft tissue investigation during minimally invasive surgery," 2008, pp. 827-830.
Dupont et al., "Design and Control of Concentric-Tube Robots.," IEEE transactions on robotics : a publication of the IEEE Robotics and Automation Society, vol. 26, No. 2, pp. 209-225, Apr. 2010.
Edwards et al., Annual report to the nation on the status of cancer, 1975-2006, featuring colorectal cancer trends and impact of interventions (risk factors, screening, and treatment) to reduce future rates. Cancer, pp. 544-574, 2010.
Egorov et al., "Mechanical Imaging of the Breast," vol. 27, No. 9, pp. 1275-1287, 2008.
Egorov et al., "Prostate mechanical imaging: 3-D image composition and feature calculations," vol. 25, No. 10, pp. 1329-1340, 2006.
Eickoff et al., Computer-assisted colonoscopy (the NeoGuide endoscopy system): results of the firsthuman clinical trial (pace study). The American Journal of Gastroenterology, 102:261-266, 2007.
Faigel, Endoscopic Oncology: Gastrointestinal Endoscopy and Cancer Management. Humana Press, 2006.
Ferlay et al., "Globocan 2012, Cancer Incidence and Mortality Worldwide: IARC CancerBase," 2013.
Ferreira et al., "Fluorescence and diffuse reflectance spectroscopy for early cancer detection using a new strategy towards the development of a miniaturized system," IEEE Engineering in Medicine and Biology Society. Conference. 2010. 1210-3.
Ferro et al., "Worldwide Trends in Gastric Cancer Mortality (1980-2011), with Predictions to 2015, and Incidence by Subtype," Eur. J. Cancer, vol. 50, No. 7, pp. 1330-44, May 2014.
Fleming et al., The safety of helium for abdominal insufflation. Surgical Endoscopy, 11:230-234 230-234, 1997.
Fritscher-Ravens et al., Cathcam guide wire-directedcolonoscopy: first pilot study in patients with a previous incomplete colonoscopy. Endoscopy, 38:209-213, 2006.
Fritscher-Ravens et al., Colon cleaning during colonoscopy: a new mechanical cleaning device tested in a porcine model. Gastrointestinal Endoscopy, 63:141-143, 2006.
Fuller et al., "Laparoscopic trocar injuries: A report from a U.S. Food and Drug Administration (FDA) Center for Devices and Radiological Health (DRH) Systematic Technology Assessment of Medical Products (STAMP) committee," 2003, www.fda.gov/medicaldevices/safety/alertsandnotices/ucm197339.htm, 16 pages.
Furlani, Permanent Magnet and Electromechanical Devices. Academic Press, 2001, pp. 131-135.
Goldman et al., "Algorithms for autonomous exploration and estimation in compliant environments," Robotica, 2012; 1-17.
Goldman et al., "Analysis , Algorithms , and Control for Intelligent Surgical Exploration and Intervention," Ph.D. Dissertation, (Advisor: N. Simaan), Mechanical Engineering, Columbia University, 2011; 1-148.
Goldman et al., "Compliant Motion Control for Continuum Robots with Intrinsic Actuation Sensing," in IEEE International Conference on Robotics and Automation, 2011, pp. 1126-1132.
Goldman et al., "Design and Performance Evaluation of a Minimally Invasive Telerobotic Platform for Transurethral Exploration and Intervention," IEEE Trans Biomed Eng. Apr. 2013;60(4):918-25.
Gorlewicz et al., "Mesoscale Mobile Robots for Gastrointestinal Minimally Invasive Surgery (MIS)", Chapter 10, pp. 224-251, in "Medical Robotics—Minimally Invasive Surgery" edited by Paula Gomes, Woodhead Publishing Series in Biomaterials: No. 51, ISBN 0-85709-130-1 (Aug. 2012).
Gorlewicz et al., "Wireless Insufflation of the Gastrointestinal Tract", IEEE Transactions on Biomedical Engineering, 2013, vol. 60, N. 5, pp. 1225-1233.
Gwilliam et al., "Human vs. robotic tactile sensing: Detecting lumps in soft tissue," in IEEE Haptics Symposium, 2010, pp. 21-28.
Hall, Guyton and Hall Textbook of Medical Physiology, 2010.

(56) References Cited

OTHER PUBLICATIONS

Horeman et al., "The Influence of Instrument Configuration on Tissue Handling Force in Laparoscopy", Surgical Innovation, 2013, vol. 20, N. 3, pp. 260-267.

Howe et al., "Remote palpation technology," IEEE Eng. Med. Biol. Mag., vol. 14, No. 3, pp. 318-323, 1995.

Inadomi et al., Adherence to colorectal cancer screening: A randomized clinical trial of competing strategies. Archives of Internal Medicine, 172(7):575-582, 2012.

Intuitive Surgical website: www.intuitivesurgical.com.

Janssens et al., Carbon dioxide for gut distension duringdigestive endoscopy: Technique and practice survey. World Journal of Gastroenterology, 15(12):1475-1479, 2009.

Kapoor et al., "Suturing in Confined Spaces: Constrained Motion Control of a Hybrid 8-DoF Robot", in IEEE International Conference on Advanced Robotics, 2005, 452-459.

Kapoor et al., "Telemanipulation of Snake-Like Robots for Minimally Invasive Surgery of the Upper Airway," in MICCAI 2006 workshop on medical robotics, 2006, 9 pages.

Keller et al., "Method for Navigation and Control of a Magnetically Guided Capsule Endoscope in the Human Stomach," Proc. of the IEEE RAS and EMBS Int. Conf. on Biomedical Robotics and Biomechatronics, pp. 859-865, 2012.

Keller et al., Inspection of the human stomach using remote controlled capsule endoscopy: a feasibility study in healthy volunteers. Gastrointestinal Endoscopy,73:22-28, 2011.

Kong et al., "A rotational micro biopsy device for the capsule endoscope," Intelligent robots and systems. In Intelligent Robots and Systems, 2005; 1839-1843.

Koulaouzidis et al., "Capsule Endoscopy in Clinical Practice: Concise Up-To-Date Overview." Clinical and Experimental Gastroenterology, vol. 2, pp. 111-116, Jan. 2009.

Kucuk et al., "Chapter 4. Robot Kinematics: Forward and Invers Kinematics," Industrial Robotics; Theory, Modeling and Control, textbook edited by Sam Cubero, published 2006, by Pro Literatur, Germany.

Kuebler et al., "Development of actuated and sensor integrated forceps for minimally invasive robotic surgery," The International Journal of Medical Robotics and Computer Assisted Surgery, vol. 1, No. 3, pp. 96-107, 2005.

Kunkel et al., "Using robotic systems in order to determine biomechanical properties of soft tissues," in Studies in Health Technology and Informatics, Proceedings of the 2nd Conference on Applied Biomechanics, vol. 133, No. 3, 2008, p. 156.

Laulicht et al., "Localization of magnetic pills," Proceedings of the National Academy of Sciences, vol. 108, No. 6, pp. 2252-2257, 2011.

Lederman et al., "Force variability during surface contact with bare finger or rigid probe," 12th International Symposium on Haptic Interfaces for Virtual Environment and Teleoperator Systems, 2004. HAPTICS '04. Proceedings., pp. 154-160, 2004.

Lee et al., "Gastric Cancer Screening and Subsequent Risk of Gastric Cancer: A Large-Scale Population-Based Cohort Study, with a 13-Year Follow-Up in Japan," Int. J. Cancer, vol. 118, No. 9, pp. 2315-2321, May 2006.

Lehman et al., "Surgery with Cooperative Robots," Comput. Aided. Surg., 13(2), pp. 95-105 (Mar. 2008).

Leung et al., "Impact of a novel water method on scheduled unsedated colonoscopy in U.S. veterans," Gastrointestinal Endoscopy, 69(3, Part 1):546-550, 2009.

Li et al.,"Diagnostic value of fecal tumor m2-pyruvate kinase for cm screening: a systematic review and meta-analysis," Int J Cancer. Oct. 15, 2012;131(8):1837-45.

Lister et al., "Development of in vivo constitutive models for liver: Application to surgical simulation," Annals of Biomedical Engineering, vol. 39, pp. 1060-1073, 2011.

Liu et al., "A haptic probe for soft tissue abnormality identification during minimally invasive surgery," 2009, pp. 417-422.

Liu et al., "Experimental study of soft tissue recovery using optical fiber probe," 2007, pp. 516-521.

Liu et al., "Rolling indentation probe for tissue abnormality identification during minimally invasive surgery," IEEE Trans. Robot., vol. 27, No. 3, pp. 450-460, 2011.

Liu et al., "Rolling Mechanical Imaging: A Novel Approach for Soft Tissue Modeling and Identification during Minimally Invasive Surgery," 2008, pp. 845-849.

Macrae et al., Towards safer colonoscopy: a report on thecomplications of 5000 diagnostic or therapeutic colonoscopies. Gut, 24(5):376-383, 1983.

Makuuchi et al., "Endoscopic Screening for Esophageal Cancer in 788 Patients with Head and Neck Cancers," The Tokai Journal of Experimental and Clinical Medicine, vol. 21, pp. 139-145, 1996.

Mayo Clinic Health System, "EGD—Mayo Clinic Health System," 2013. [Online]. Available: http://mayoclinichealthsystem.org/locations/eau-claire/medical-services/gastroenterology-and-hepatology/egd.

Seidell, Solubilities of inorganic and organic substances. New York, D. Van Nostrand company, 2nd edition, 1907.

Shaker et al., Principles of Deglutition. Springer Science & Business Media, 2012.

Shike et al., Sightline Colonsight system for a disposable, power-assisted, non-fiber-optic colonoscopy. Gastrointestinal Endoscopy, 68:701-710, 2008.

Sieber et al., "A Novel Haptic Platform for Real Time Bilateral Biomanipulation with a MEMS Sensor for Triaxial Force Feedback", Sensors and Actuators A: Physical, 2008, vol. 142, No. 1, pp. 19-27.

Sieber et al., "Flip Chip Microassembly of a Silicon Triaxial Force Sensor on Flexible Substrates", Sensors and Actuators A: Physical, 2008, vol. 142, No. 1, pp. 421-428.

Silvestri et al., "Comparative study on surgical performance between two- and three-dimensional vision systems and interfaces", Surgical Innovation, 2011, vol. 18, No. 3, pp. 223-230.

Simaan et al., "Design and Integration of a Telerobotic System for Minimally Invasive Surgery of the Throat," International Journal of Robotics Research—special issue on Medical Robotics (special Issue on Medical Robotics), vol. 28, No. 9, pp. 1134-1153, 2009.

Simaan, "Snake-Like Units Using Flexible Backbones and Actuation Redundancy for Enhanced Miniaturization," in IEEE International Conference on Robotics and Automation, 2005, pp. 3020-3028.

Simi et al., "Design, Fabrication and Testing of an Endocapsule with Active Hybrid Locomotion for the Exploration of the Gastrointestinal Tract", IEEE Transactions on Mechatronics, 2010, vol. 15, No. 2, pp. 170-180.

Simi et al., "Fine tilt tuning of a laparoscopic camera by local magnetic actuation: Two-Port Nephrectomy Experience on Human Cadavers", Surgical Innovation, 2013, vol. 20, N. 4, pp. 385-394.

Simi et al., "Magnetic Levitation Camera Robot for Endoscopic Surgery", in Proc. of IEEE International Conference on Robotics and Automation (ICRA) 2011, Shanghai, China, May 2011, pp. 5279-5284.

Simi et al., "Magnetic link design for a robotic laparoscopic camera", Journal of Applied Physics, 2010, vol. 107, No. 9, pp. 09B302-09B302-3.

Simi et al., "Magnetic Mechanism for Wireless Capsule Biopsy", in Proc. of ASME Design of Medical Devices conference, Apr. 10-12, 2012, Minneapolis, MN, ASME Journal of Medical Devices, vol. 6, p. 017611-1.

Simi et al., "Magnetic Torsion Spring Mechanism for a Wireless Biopsy Capsule", ASME Journal of Medical Devices, 2013, in press.

Simi et al., "Magnetically Activated Stereoscopic Vision System for Laparoendoscopic Single Site Surgery", IEEE/ASME Transactions on Mechatronics, 2013, vol. 18, N. 3, pp. 1140-1151.

Simi et al., "Modeling of a Compliant Joint in a Magnetic Levitation System for an Endoscopic Camera", Mechanical Sciences, 2012, vol. 3, pp. 5-14.

Smith, Byron, "Wireless Insufflation for Wireless Capsule Endoscopy," Vanderbilt University Master's Thesis (Aug. 2012).

Song et al., "Mechanical properties of the human abdominal wall measured in vivo during insufflation for laparoscopic surgery," Surgical Endoscopy, vol. 20, No. 6, pp. 987-990, 2006.

(56) References Cited

OTHER PUBLICATIONS

Sonnenberg et al., "Is virtual colonoscopy a cost-effective option to screen for colorectal cancer?" Am J Gastroenterol. Aug. 1999;94(8):2268-74.
Sosna et al., "Colonic perforation at CT colonography:assessment of risk in a multicenter large cohort," Radiology. 2006; 239(2):457-63.
Stark et al., "The future of telesurgery: a universal system with haptic sensation," Journal of the Turkish-German Gynecological Association, vol. 13, No. 1, pp. 74-76, 2012.
Stevension, "Pain following colonoscopy: elimination with carbon dioxide," Gastrointestinal Endoscopy, pp. 564-567, 1992.
Sumanac et al., Minimizing postcolonoscopy abdominal pain by using fCO2g insufflation: Aprospective, randomized, double blind, Controlled trial evaluating a new commercially availablefCO2g delivery system. Gastrointestinal Endoscopy, 56(2):190-194, 2002.
Susilo et al., "A Miniaturized Wireless Control Platform for Robotic Capsular Endoscopy Using Advanced Pseudokernel Approach", Sensors and Actuators A: Physical, 2009, vol. 156, No. 1, pp. 49-58.
Swain et al., Development and testing of a tethered, independent camera for NOTES and single-site laparoscopic procedures. Surgical Endoscopy, 24:2013-2021, 2010.
Takktile by Y. Tenzer, L Jentoft, I. Daniher, and Robert Howe: www.takktile.com, 2013, 1 page.
Than et al., "A Review of Localization Systems for Robotic Endoscopic Capsules," Biomedical Engineering, IEEE Transactions on , vol. 59, No. 9, pp. 2387-2399, Sep. 2012.
The Center for Disease Control and Prevention, "Colorectal cancer screening basic fact sheet," 2017, 2 pages.
Tholey et al., "A compact and modular laparoscopic grasper with tri-directional force measurement capability," ASME Journal of Medical Devices, vol. 2, No. 3, pp. 031 001-9, 2008.
Toennies et al., "Initial Feasibility Studies on Wireless Insufflation of the GI Tract," IEEE International Conference on Robotics and Automation 2010—Workshop on Meso-ScaleRobotics for Medical Interventions, (May 3, 2010).
Toennies et al., "Swallowable Medical Devices for Diagnosis and Surgery: The State of the Art", Proceedings of the Institution of Mechanical Engineers, Part C: Journal of Mechanical Engineering Science, 2010, vol. 224, No. 7, pp. 1397-1414.
Toennies et al., "Toward Tetherless Insufflation of the GI Tract", in Proc. IEEE Engineering in Medicine and Biology Society Conference (EMBC) 2010, Buenos Aires, Argentina, Sep. 2010, pp. 1946-1949.
Toennies et al., A wireless insufflation system for capsular endoscopes. ASME Journal of Medical Devices, 3 (2):27514, 2009.
Tognarelli et al., "A pilot study on a new anchoring mechanism for surgical applications based on mucoadhesives", Minimally Invasive Therapy & Allied Technologies, 2011, vol. 20, No. 1, pp. 3-13.
Tonet et al., "Control of a teleoperated nanomanipulator with time delay under direct vision feedback", in Proc. of IEEE International Conference on Robotics and Automation (ICRA) 2007, Rome, Italy, Apr. 2007, pp. 3514-3519.
Tortora et al., "Design of an autonomous jellyfish miniature robot based on a novel concept of magnetic actuation", in Proc. of IEEE International Conference on Robotics and Automation (ICRA) 2010, Anchorage, AK, USA, May 2010, pp. 1592-1597.
Tortora et al., "Propeller-based wireless device for active capsular endoscopy in the gastric district", Minimally Invasive Therapy & Allied Technologies, 2009, vol. 18, No. 5, pp. 280-290.
Tully et al., "Constrained Filtering with Contact Detection Data for the Localization and Registration of Continuum Robots in Flexible Environments," Proceedings—IEEE International Conference on Robotics and Automation, 2012, 3388-3394.
Turchetti et al., "The importance of giving an alternative: the case of fetal surgery", Int. J. Healthcare Technology and Management, 2007, vol. 8, Nos. 3-4, pp. 250-267.
Valdastri et al., "A Magnetic Internal Mechanism for Camera Steering in Wireless Endoluminal Applications", Endoscopy, 2010, vol. 42, pp. 481-486.

Valdastri et al., "A New Mechanism for Meso-Scale Legged Locomotion in Compliant Tubular Environments", IEEE Transactions on Robotics, 2009, vol. 25, No. 5, pp. 1047-1057.
Valdastri et al., "A novel magnetic actuation system for miniature swimming robots", IEEE Transactions on Robotics, 2011, vol. 27, No. 4, pp. 769-779.
Valdastri et al., "A scalable platform for biomechanical studies of tissue cutting forces", Measurement Science and Technology, 2009, vol. 20, 045801 (11pp).
Valdastri et al., "Advanced Technologies for Gastrointestinal Endoscopy," Annu. Review of Biomed. Eng., vol. 14, pp. 397-429, 2012.
Valdastri et al., "An Implantable Telemetry Platform System for in vivo Monitoring of Physiological Parameters", IEEE Transactions on Information Technology in Biomedicine, 2004, vol. 8, No. 3, pp. 271-278.
Valdastri et al., "An Implantable ZigBee Ready Telemetric Platform for in Vivo Monitoring of Physiological Parameters", Sensors and Actuators A: Physical, 2008, vol. 142, No. 1, pp. 369-378.
Valdastri et al., "Characterization of a novel hybrid silicon three-axial force sensor", Sensors and Actuators A: Physical, 2005, vol. 123-124C, pp. 249-257.
Valdastri et al., "Integration of a Miniaturised Triaxial Force Sensor in a Minimally Invasive Surgical Tool", IEEE Transactions on Biomedical Engineering, 2006, vol. 53, No. 11, 2397-2400.
Valdastri et al., "Magnetic air capsule robotic system: a novel approach for painless colonoscopy", 19th International Congress of the European Association of Endoscopic Surgery (EAES) in Turin, Italy, 2011, 1 page.
Valdastri et al., "Magnetic air capsule robotic system: Proof of concept of a novel approach for painless ,mlonoscopy", Surgical Endoscopy, 2012, vol. 26, N. 5, pp. 1238-1246.
Chinese Patent Office Action for Application No. 201580060855.6 dated Jul. 3, 2018, 8 pages. No translation.
European Patent Office Search Report for Application No. 15840650.4 dated May 28, 2018, 8 pages.
PCT International Search Report and Written Opinion for Application No. PCT/EP2011/064764 dated Oct. 10, 2011.
PCT International Search Report and Written Opinion for Application No. PCT/IB2012/052739 dated Aug. 7, 2012.
PCT International Search Report and Written Opinion for Application No. PCT/US2014/012086 dated May 14, 2014.
PCT International Search Report and Written Opinion for Application No. PCT/US2014/60324 dated Jan. 11, 2015, 8 pages.
PCT International Search Report and Written Opinion for Application No. PCT/US2015/049142 dated Dec. 11, 2015.
Adami et al., "Primary and Secondary Prevention in the Reduction of Cancer Morbidity and Mortality." Eur. J. Cancer, vol. 37 Suppl 8, pp. S118-S127, 2001.
Alonso et al., "Enabling multiple robotic functions in an endoscopic capsule for the entire gastrointestinal tract exploration", in Proc. ESSCIRC, 2010, pp. 386-389.
American Cancer Society, "Cancer Facts & Figures 2005," 2005.
American Cancer Society, "What are the key statistics about colorectal cancer?" http://www.cancer.org/Cancer/ColonandRectumCancer/DetailedGuide/colorectal-cancer-key-statistics. Jun. 2012, 1 page.
Arber et al., Proof-of-concept study of the aer-o-scope omnidirectional colonoscopic viewing system in ex vivo and in vivo porcine models. Endoscopy, 39(5):412-417, May 2007.
Arezzo et al., "Experimental assessment of a novel robotically-driven endoscopic capsule compared to traditional colonoscopy", Digestive and Liver Disease, 2013, vol. 45, N. 8, pp. 657-662.
Ascari et al., "A New Active Microendoscope for Exploring the Subarachnoid Space in the Spinal Cord," 2003 IEEE Int. Conf. Robot. Autom., vol. 2, pp. 2657-2667, 2003.
Bajo et al., "Configuration and Joint Space Feedback for Improved Accuracy of Continuum Robots," in IEEE International Conference on Robotics and Automation, 2011, pp. 2905-2912.
Bajo et al., "Finding Lost Wrenches: Using Continuum Robots for Contact Detection and Estimation of Contact Location," in 2010 IEEE International Conference on Robotics and Automation, 2010, pp. 3666-3673.

(56) References Cited

OTHER PUBLICATIONS

Bajo et al., "Integration and Preliminary Evaluation of an Insertable Robotic Effectors Platform for Single Port Access Surgery," IEEE International Conference on Robotics and Automation, Saint Paul, MN, 2012, pp. 3381-3387.
Bajo et al., "Kinematics-Based Detection and Localization of Contacts Along Multisegment Continuum Robots," IEEE Transactions on Robotics, 2012; 28(2): 291-302.
Beccai et al., "Design and fabrication of a hybrid silicon three axial force sensor for biomechanical applications", Sensors and Actuators A: Physical, 2005, vol. 120, No. 2, pp. 370-382.
Beccai et al., "Development and Experimental Analysis of a Soft Compliant Tactile Microsensor to be Integrated in an Antropomorphic Artificial Hand", IEEE/ASME Transactions on Mechatronics, 2008, vol. 13, No. 2, pp. 158-168.
Beccani et al., "Uniaxial Wireless Tissue Palpation Device for Minimally Invasive Surgery", ASME Design of Medical Devices Conference, Apr. 2013, Minneapolis, Minnesota, ASME Journal of Medical Devices, vol. 7, N. 2, 020919 (3 pp).
Beccani et al., "Wireless Tissue Palpation for Intraoperative Detection of Lumps in Soft Tissue", IEEE Transactions on Biomedical Engineering, 2013, in press 9 pages.
Beccani et al., "Wireless Tissue Palpation: Proof of Concept for a Single Degree of Freedom", IEEE International Conference on Robotics and Automation (ICRA) 2013, Karlsruhe, Germany, pp. 703-709.
Bell et al., "Image partitioning and illumination in image-based pose detection for teleoperated flexible endoscopes", Artificial Intelligence in Medicine, 2013, in press, 12 pages.
Best et al., New generation magnetic camera facilitates porcine LESS nephrectomy. The Journal of Urology, 185: e413-e413, 2011.
Bhattacharyya, "Motion Planning and Constraint Exploration for Robotic Surgery," M.Sc. thesis, (Advisor: N. Simaan), Mechanical Engineering, Vanderbilt University, 2011; 1-130.
Bracco, "Co2 efficient endoscopic insufflator," http://imaging.bracco.com/us-en/products-and-solution/endoscopy/co2efficient-insufflator, 3 pages.
Bray et al., "Global Cancer Transitions According to the Human Development Index: A Population-Based Study," The Lancet Oncology,2012; 13: 790-801.
Burgner et al., "A bimanual teleoperated system for endonasal skull base surgery," in 2011 IEEE/RSJ International Conference on Intelligent Robots and Systems, 2011, pp. 2517-2523.
Burling et al., Automated Insufflation of Carbon Dioxide for Mdct Colonography: Distension and Patient Experience Compared with Manual Insufflation. Journal of Radiology, 2006; 186: 96-103.
Buselli et al., "Evaluation of friction enhancement through soft polymer micro-patterns in active capsule endoscopy", Measurement Science and Technologies, 2010, 21 105802 (7pp).
Buselli et al., "Superelastic leg design optimization for an endoscopic capsule with active locomotion", Smart Materials and Structures, 2009, vol. 18, 015001 (8pp).
Cadeddu et al., "Novel magnetically guided intra-abdominal camera to facilitate laparoendoscopic single site surgery: initial human experience," Surg. Endoscopy, 23, pp. 1894-1899 (May 9, 2009).
Carpi et al., Magnetically controllable gastrointestinal steering ofvideo capsules. IEEE Transactions on Biomedical Engineering, 58:231-234, 2011.
Carta et al., "Wireless powering for a self-propelled and steerable endoscopic capsule for stomach inspection", Biosensors and Bioelectronics, 2009, vol. 25, No. 4, pp. 845-851.
Cavallotti et al., "An FPGA-based flexible demo-board for endoscopic capsule design optimization", Sensors and Actuators A: Physical, 2011, vol. 172, No. 1, pp. 301-307.
Cavallotti et al., "An Integrated Vision System with Autofocus for Wireless Capsular Endoscopy", Sensors and Actuators A: Physical, 2009, vol. 156, No. 1, pp. 72-78.
Chiang et al., "Tendon Sheath Analysis for Prediction of Distal End Force and Elongation", in Proc. IEEE/ASME Conference on Advanced Intelligent Mechatronics 2009, Singapore, Jul. 2009, pp. 332-337.
Ciuti et al., "A Comparative Evaluation of Control Interfaces for a Robotic-Aided Endoscopic Capsule Platform", IEEE Transactions on Robotics, 2012, vol. 28, N. 2, pp. 534-538.
Ciuti et al., "A wireless module for vibratory motor control and inertial sensing in capsule endoscopy", Sensors and Actuators A: Physical, 2012, vol. 186, pp. 270-276.
Ciuti et al., "Robotic magnetic steering and locomotion of capsule endoscope for diagnostic and surgical endoluminal procedures", Robotica, 2010, vol. 28, No. 2, pp. 199-207.
Ciuti et al., "Robotic versus manual control in magnetic steering of an endoscopic capsule", Endoscopy, 2010, vol. 42, pp. 148-152.
Clark, Anatomy and Physiology: Understanding the Human Body. Sudbury,MA: Jones and Bartlett, 2005.
Classen, Gastroenterological Endoscopy. Thieme Medical Publishers, 2010.
Conway et al., "Endoscopic hemostatic devices," Gastrointest Endosc. 2009; 69(6):987-96.
Cosentino et al., Functional evaluation of theEndotics System, a new disposable self-propelled robotic colonoscope: in vitro tests and clinical trial.International Journal of Artificial Organs, 32:517-527, 2009.
Covi et al., "Miniaturized digital camera system for disposable endoscopic applications", Sensors and Actuators A: Physical, 2010, vol. 162, No. 2, pp. 291-296.
Culmer et al., "Reviewing the technological challenges associated with the development of a laparoscopic palpation device," The International Journal of Medical Robotics and Computer Assisted Surgery, vol. 8, No. 2, pp. 146-159, 2012.
Dario et al., "An advanced robot system for automated diagnostic tasks through palpation," IEEE Trans. Biomed. Eng., vol. 35, No. 2, pp. 118-126, 1988.
Davila et al., ASGE guideline: colorectal cancer screening and surveillance, American Society for Gastrointestinal Endoscopy, 2006; 63(4): 546-557.
De Falco et al., "An Integrated System for Wireless Capsule Endoscopy in a Liquid-Distended Stomach," IEEE Trans. Biomed. Eng., vol. 61, No. 3, pp. 794-804, Mar 2013.
Dellon et al., "The use of carbon dioxide for insufflation during GI endoscopy: a systematic review Gastrointestinal Endoscopy," 69:843-849, 2009.
Di Natali et al., "Real-Time Pose Detection for Magnetic Medical Devices", IEEE Transactions on Magnetics, 2013, vol. 49, N. 7, pp. 3524-3527.
Di Natali et al., "Remote active magnetic actuation for a single-access surgical robotic manipulator", in Proc of the XVI Annual Conference of the International Society for Computer Aided Surgery (ISCAS) 2012, Pisa, Italy, Jun. 2012, International Journal of Computer Assisted Radiology and Surgery, 2012, vol. 7, Suppl. 1, pp. S169-S170.
Di Natali et al., "Trans-abdominal Active Magnetic Linkage for Robotic Surgery: Concept Definition and Model Assessment", in Proc. Of IEEE International Conference on Robotics and Automation (ICRA) 2012, St Paul, MN, USA, May 2012, pp. 695-700.
Dietzel et al., "Magnetic active agent release system (maars): Evaluation of a new way for a reproducible, externally controlled drug release into the small intestine," J Control Release. Aug. 10, 2012;161(3):722-7.
Mccreery et al., "Feasibility of locating tumours in lung via kinaesthetic feedback." The International Journal of Medical Robotics and Computer Assisted Surgery, vol. 4, No. 1, pp. 58-68, 2008.
Menciassi et al., "Single and Multiple Robotic Capsules for Endoluminal Diagonosis and Surgery", Chapter 14, pp. 313-354, in "Surgical Robotics—System Applications and Visions", edited by J. Rosen, B. Hannaford, R. Satava, published by Springer, 1st Edition, 2011, XXII, 819 p. 365 illus, Hardcover, ISBN: 978-1-4419-1125-4.
Miller et al., "Tactile imaging system for localizing lung nodules during video assisted thoracoscopic surgery," 2007, pp. 2996-3001.
Mishkin et al., "ASGE Technology Status Evaluation Report: Wireless Capsule Endoscopy." Gastrointestinal Endoscopy, vol. 63, No. 4, pp. 539-545, Apr. 2006.
Misra et al., "Environment Parameter Estimation during Bilateral Telemanipulation," in IEEE Virtual Reality Conference (VR'06), 2006, No. 1, pp. 301-307.

(56) References Cited

OTHER PUBLICATIONS

Moll et al., "Reconstructing shape from motion using tactile sensors," 2001, vol. 2, pp. 692-700.

Moshkowitz et al., A novel device for rapid cleaning of poorly prepared colons. Endoscopy, 42:834-836, 2010.

Naish et al., "Effect of Velocity Control on Kinesthetic Lung Tumour Localization," in 21st Canadian Conference on Electrical and Computer Engineering, 2008, vol. 1345, pp. 1337-1340.

National Digestive Diseases Information Clearinghouse, https://www.niddk.nih.gov/health-information/digestive-diseases.

NDI Medical's Aurora product, http://www.ndigital.com/medical/products/aurora/, publicly available prior to Sep. 17, 2012, 6 pages.

Noonan et al., "A dual-function wheeled probe for tissue viscoelastic property identification during minimally invasive surgery," 2007, pp. 2629-2634.

Obstein et al., "Advanced Endoscopic Technologies for Colorectal Cancer Screening", World Journal of Gastroenterology, 2013, vol. 19, N. 4, pp. 431-439.

Obstein et al., "Novel approach for colonic insufflation via an untethered capsule (with video)", Gastrointestinal Endoscopy, 2013, vol. 77, N. 3, pp. 516-517.

Oddo et al., "Investigation on calibration methods for multi-axis, linear and redundant force sensors", Measurement Science and Technology, 2007, vol. 18, pp. 623-631.

Ohtsuka et al., "Application of a new tactile sensor to thoracoscopic surgery: Experimental and clinical study," The Annals of Thoracic Surgery, vol. 60, No. 3, pp. 610-614, 1995.

Okamura et al., "Feature Guided Exploration with a Robotic Finger," 2001, pp. 589-596.

Okamura et al., "Overview of dexterous manipulation," 2000, vol. 1, pp. 255-262.

Oshima et al., "Evaluation of a Mass Screening Program for Stomach Cancer with a Casecontrol Study Design," Int. J. Cancer, vol. 38, No. 6, pp. 829-33, Dec. 1986.

Ostrovsky, Preview of Magnetically Guided Colonoscopy from Vanderbilt. MedGadget press release:http://medgadget.com/2011/10/preview-of-magnetically-guided-colon-oscopy-from-vanderbilt.html., 6 pages.

Ottensmeyer et al., "In vivo data acquisition instrument for solid organ mechanical property measurement," in Medical Image Computing and Computer-Assisted Intervention—MICCAI 2001 Springer, 2001, pp. 975-982.

Park et al., Trocar-less instrumentation for laparoscopy: magnetic positioning of intra-abdominal camera and retractor. Annals of Surgery,245:379-384, 2007.

Patterson et al., "The Pig as an Experimental Model for Elucidating the Mechanisms Governing Dietary Influence on Mineral Absorption," Experimental biology and medicine, 2008; 233(6):651-64.

Pedersen, "Capsule Endoscopy in ER Could Drop Admission Rate," Medical Device Daily (Feb. 13, 2013).

Pensabene et al., "Mucoadhesive film for anchoring assistive surgical instruments in endoscopic surgery: in vivo assessment of deployment and attachment", Surgical Endoscopy, 2011, vol. 25, No. 9, pp. 3071-3079.

Phaosawasdi et al., Carbon dioxide-insufflated colonoscopy: an ignoredsuperior technique. Gastrointestinal Endoscopy, 32:330-333, 1986.

Piccigallo et al., "Design of a novel bimanual robotic system for single-port laparoscopy", IEEE/ASME Transactions on Mechatronics, 2010, vol. 15, No. 6, pp. 871-878.

PillCam Capsule Endoscopy products by Given Imaging, http://www.givenimaging.com/en-int/Innovative-Solutions/Capsule-Endoscopy-/Pages/default.aspx, available prior to Sep. 17, 2012.

Pilz et al., "Colon capsule endoscopy compared to conventional colonoscopy under routine screening conditions," BMC Gastroenterology, 2010; 10:66.

Puangmali et al., "Miniature 3-axis distal force sensor for minimally invasive surgical palpation," IEEE/ASME Trans. Mechatronics, vol. 17, No. 4, pp. 646-656, 2012.

Puangmali et al., "Optical Fiber Sensor for Soft Tissue Investigation during Minimally Invasive Surgery," in 2008 IEEE International Conference on Robotics and Automation, 2008, pp. 2934-2938.

Quaglia et al., "An Endoscopic Capsule Robot: A Meso-Scale Engineering Case Study", Journal of Micromechanics and Microengineering, 2009, vol. 19, No. 10, 105007 (11pp).

Duirini et al., Feasibility proof of a legged locomotion capsule for the GI tract. Gastrointestinal Endoscopy, 67:1153-1158, 2008.

Randolph et al., "Recurrent laryngeal nerve identification and assessment during thyroid surgery: laryngeal palpation," World journal of surgery, vol. 28, No. 8, pp. 755-60, Aug. 2004.

Ranzani et al., "A Novel Surgical Robotic Platform Minimizing Access Trauma", in Proc. of 4th Hamlyn Symposium on Medical Robotics, London, UK, Jun. 2011, pp. 15-16.

Rey et al., Feasibility of stomach exploration with a guided capsule endoscope. Endoscopy, 42:541-545, 2010.

Richert et al., "Magnetic sensor techniques for new intelligent endoscopic capsules," http://www.vector-project.com/press/artikel/VECTOR%20article.sub.--Richer-t.sub.-MagneticSensorTechniques.pdf, publicly available prior to Sep. 17, 2012, 6 pages.

Rogers, The safety of carbon dioxide insufflation during colonoscopic electro-surgical polypectomy. Gastrointestinal Endoscopy, 20:115-117, 1974.

Rösch et al., A motor-driven single-use colonoscope controlled with a hand-held device: a feasibility study involunteers. Gastrointestinal Endoscopy, 67:1139-1146, 2008.

Rosen et al., "Biomechanical properties of abdominal organs in vivo and postmortem under compression loads," Journal of Biomechanical Engineering, vol. 130, No. 021020, pp. 1-17, 2008.

Rucker et al., "A Geometrically Exact Model for Externally Loaded Concentric-Tube Continuum Robots.," IEEE transactions on robotics : a publication of the IEEE Robotics and Automation Society, vol. 26, No. 5, pp. 769-780, Jan. 2010.

Rucker et al., "Computing Jacobians and compliance matrices for externally loaded continuum robots," in 2011 IEEE International Conference on Robotics and Automation, 2011, No. 3, pp. 945-950.

Rucker et al., "Equilibrium Conformations of Concentric-tube Continuum Robots," The International Journal of Robotics Research, vol. 29, No. 10, pp. 1263-1280, Apr. 2010.

Sabatini et al., "Interpretation of mechanical properties of soft tissues from tactile measurements," vol. 139, 1990, pp. 152-162.

Salerno et al., "A discrete-time localization method for capsule endoscopy based on on-board magnetic sensing", Measurement Science and Technology, 2012, 23 015701 (10pp).

Samur et al., "A robotic indenter for minimally invasive measurement and characterization of soft tissue response," Medical Image Analysis, vol. 11, No. 4, pp. 361-373, 2007.

Sangpradit et al., "Tissue identification using inverse finite element analysis of rolling indentation," 2009, pp. 1250-1255.

Sauk et al., "Optical enhancements in diagnosis and surveillance of colorectal neoplasia," Curr Colorectal Cancer Rep, 2011; 7: 24-32.

Scheidler et al., Virtual colonoscopy using ct and mri. Radiologe, 38(10):824-31, 1998.

Schindler et al., "Foaming at the mouth: Ingestion of Hydrogen Peroxide Solution (with video)," Clinical gastroenterology and hepatology, Feb. 2012; 10(2): e13-4.

Segnan et al., Comparing attendance and detection rate of colonoscopy with sigmoidoscopy and FIT for colorectal aancer screening. Gastroenterology, 132(7):2304-2312, Jun 2007.

Ciuti, "Innovative control platforms for robotic microsystems in endoluminal surgery", PhD Thesis, Scuola Superiore di Studi Universitari e Perfezionamento Sant' Anna, 2012, 167 pages.

* cited by examiner

ROBOTIC CAPSULE SYSTEM WITH MAGNETIC ACTUATION AND LOCALIZATION

RELATED APPLICATIONS

This application claims the benefit of U.S. Provisional Application No. 62/569,990, filed Oct. 9, 2017, entitled "A ROBOTIC CONTROL SYSTEM FOR MAGNETICALLY ACTUATED CAPSULE ENDOSCOPES," the entire contents of which are incorporated herein by reference.

STATEMENT OF GOVERNMENT INTEREST

This invention was made with government support under grant number EB018992 awarded by the National Institutes of Health and under grant number 1453129 awarded by the National Science Foundation. The government has certain rights in the invention.

BACKGROUND

The present invention relates to systems and methods for operating a device in a cavity including, for example, endoscopic medical devices.

SUMMARY

In various embodiments, the invention enables active control of the locomotion (2 degree of freedom in position and 2 degree of freedom in orientation) of a magnetically actuated capsule endoscope. The overall system includes a robotic arm, a permanent magnet attached to said arm, and a capsule endoscope with an embedded permanent magnet and proprioceptive sensors. The system, in real-time, computes the pose (position and orientation) of the capsule using data from the sensors. The pose is used in a feedback control loop to maneuver the capsule to desired positions and orientations specified by a physician.

Some embodiments of the invention give physicians direct control and awareness of the motion of the capsule endoscope allowing for a more complete inspection of the gastrointestinal tract. The platform solves the problem of pain during colonoscopy. Due, at least in part, to the design of the soft-tethered capsule and to the way it is manipulated by magnetic fields, stretching of tissue (associated with pain and common during colonoscopy) is not expected. Specifically, the endoscopic camera is pulled from the front instead of pushed from the back. In some examples described herein, a closed-loop robotic control makes colonoscopy easy to learn and operate, differently from standard colonoscopy that requires extensive training. A user interface is also described that further reduces the learning curve.

Localization techniques are described herein that solve the problem of singularity in the magnetic field wherein, due to symmetry in the field, the capsule can be located in a number of different positions and the localization is not able to identify the correct one. As described herein, an electromagnetic coil is used to disrupt this symmetry and the unique position and orientation of the object can be identified.

In various embodiments, the systems and methods described herein can be applied to lower endoscopy (e.g., colonoscopy, flexible sigmoidoscopy, etc.), upper endoscopy, and to steering and control of magnetically actuated in-vivo robots.

In one embodiment, the invention provides a method of localizing a capsule. The capsule is positioned in a magnetic field generated by a first magnet and an electromagnetic coil is operated to generate a sinusoidal magnetic field with a magnetic moment orthogonal to the magnetic moment of the first magnet. A sequence of magnetic vector measurements is captured at a defined sampling frequency over a defined period of time for each of a plurality of magnetic field sensors coupled to the capsule. An average signal measurement is calculated for each magnetic field sensor and defined as being equal to the magnetic field applied to the magnetic field sensor by the first magnet. The magnetic field applied to the magnetic field sensor by the electromagnetic coil is then determined based, at least in part, on a difference between the magnetic vector measurements and the average signal measurement for the magnetic field sensor. The pose of the capsule is then determined based at least in part on a combination of magnetic field signals applied by the electromagnetic coil to each of the magnetic field sensors.

In another embodiment, the invention provides a system for controlling and monitoring movement of a capsule. The system includes a robotic arm, an external permanent magnet coupled to a distal end of the robotic arm, and an electromagnetic coil positioned around the external permanent magnet with a magnetic moment of the electromagnetic coil being orthogonal to a magnetic moment of the external permanent magnet. The capsule includes a plurality of magnetic field sensors positioned at different locations on the capsule and an internal permanent magnet positioned inside the capsule. A controller is configured to adjust a position of the capsule by controllably adjusting a position of the external permanent magnet. Movement of the external permanent magnet causes movement of the capsule due to magnetic attraction between the external permanent magnet and the internal permanent magnet. The controller is further configured to operate the electromagnetic coil to generate a sinusoidal magnetic field and to periodically receive signals indicative of magnetic field vectors sensed by each of the magnetic field sensors of the capsule. The controller calculates an average signal measurement for a first magnetic field sensor and determines a magnetic field signal applied by the electromagnetic coil to the first magnetic field sensor based at least in part on a difference between each magnetic field vector measurement from the first magnetic field sensor and the average signal measurement for the first magnetic field sensor. The controller then determines a pose of the capsule based at least in part on the determined magnetic field signal applied by the electromagnetic coil to the first magnetic field sensor.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
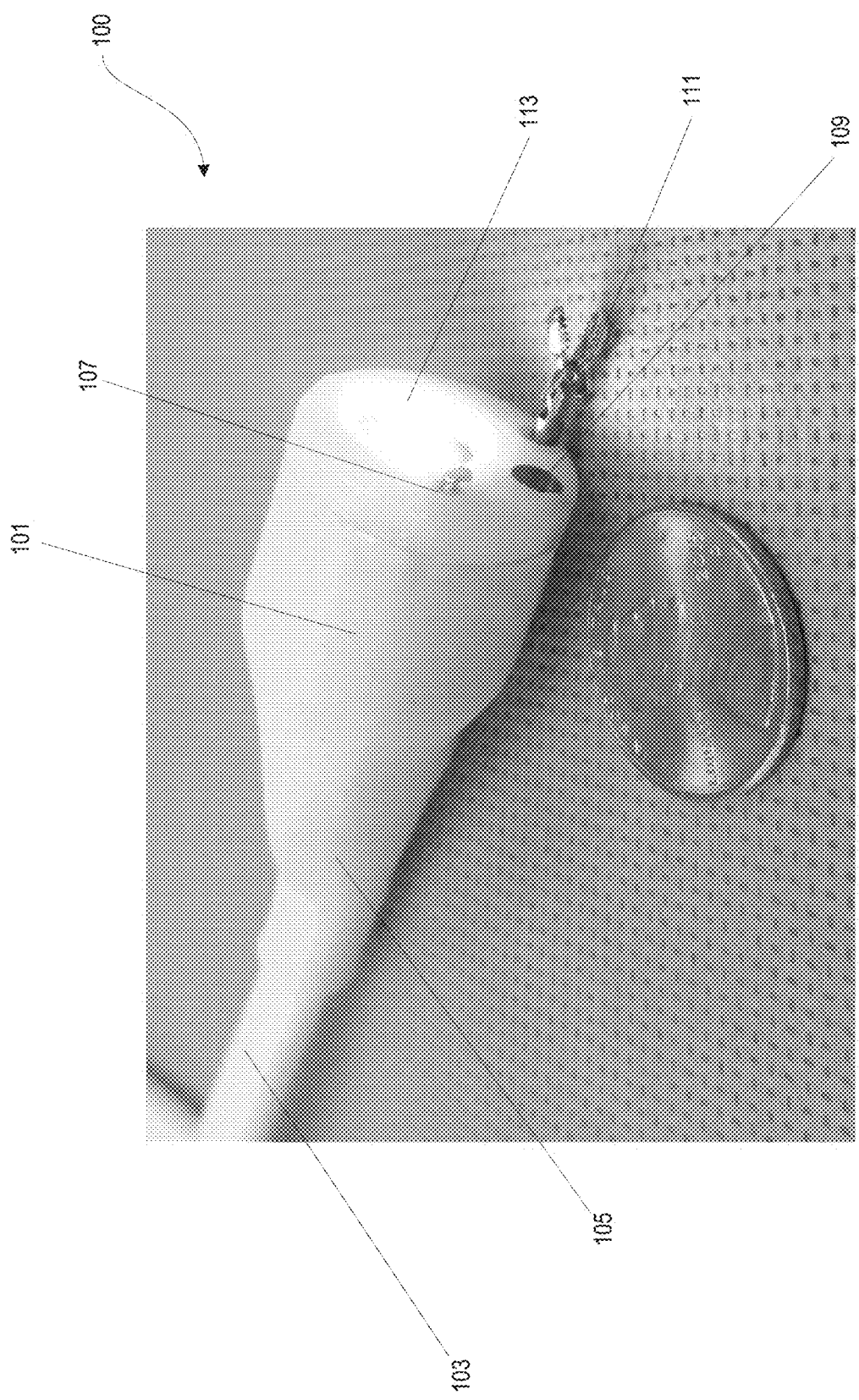
FIG. 1 is a perspective view of a distal end of a flexible endoscope including a capsule according to one embodiment.

FIG. 1 illustrates an example of an endoscope 100 with a magnet-embedded tip. The endoscope tip is provided as a capsule 101 (as described in further detail below) affixed to a distal end of a flexible endoscope body 103. A flexible sleeve 105 joins the capsule 101 with the flexible endoscope body 103. In the example of FIG. 1, the capsule 101 has a diameter of 20.6 mm while the diameter of the endoscope body 103 is 6.5 mm. The flexible sleeve 105 is sized to at least partially cover an exterior surface of the capsule 101 and an exterior surface of the endoscope body 103. The flexible sleeve 105 is also tapered to gradually reduce the diameter of the flexible sleeve 105 to tightly fit around the different diameters of the capsule 101 and the endoscope body 103. In this example, the flexible sleeve 105 is formed of a cast urethane (Elastomer 25A) material. However, in other examples, a different flexible material might be used to form the flexible sleeve 105. Because the endoscope body 103 is formed of compliant/flexible materials, the endoscope 100 is able to passively bend as the capsule 101 is advanced through a cavity (e.g., a human colon and/or intestine) until it reaches a target site. Furthermore, because the flexible sleeve 105 is also formed of a compliant/flexible material, stress and strain at the point where the endoscope body 103 meets the capsule 101 is reduced.

The capsule 101 can be adapted with various different tools including, for example, an irrigation/insufflation channel 107, a camera 109, a biopsy tool/instrument 111, and a light source 113 as shown in the example of FIG. 1. As described in further detail below, tools such as the camera 109 and the light source 113 can be positioned within the capsule 101 and receive operating power through a wired connection that runs through the endoscope body 103. Similarly, control signals and image data can be conveyed from the capsule 101 to an external system a wired connection that runs through the endoscope body 103. Mechanical tools, such as the biopsy tool 111, can be operated by electrical signals and power received through the endoscope body or the mechanical tool itself can be extended through the length of an instrument channel and operated externally at a proximal end of the endoscope body 103 (e.g., by pushing, pulling, and/or rotating rigid wires). Finally, a fluid and/or gaseous medium can be pumped through an fluid/gas channel of the endoscope body 103 from a pump and source located at the proximal end of the endoscope body 103 and emitted through the opening at the distal end of the capsule 101. Alternatively or additionally, a fluid or gas pump can be configured to apply suction to the fluid/gas channel at the proximal end of the endoscope body 103 in order to draw fluid into the opening at the distal end of the capsule from the exterior of the capsule 101. The arrangement and configuration of tools and instruments of the capsule 101 illustrated in FIG. 1 is only one example. In other implementations, the capsule 101 may be configured to utilize other tools/instruments in addition to or instead of those illustrated in FIG. 1. Furthermore, the particular arrangement of endoscope channels and the location of the tools/instruments on the exterior body of the capsule 101 may be different in other implementations.

Figure 2:
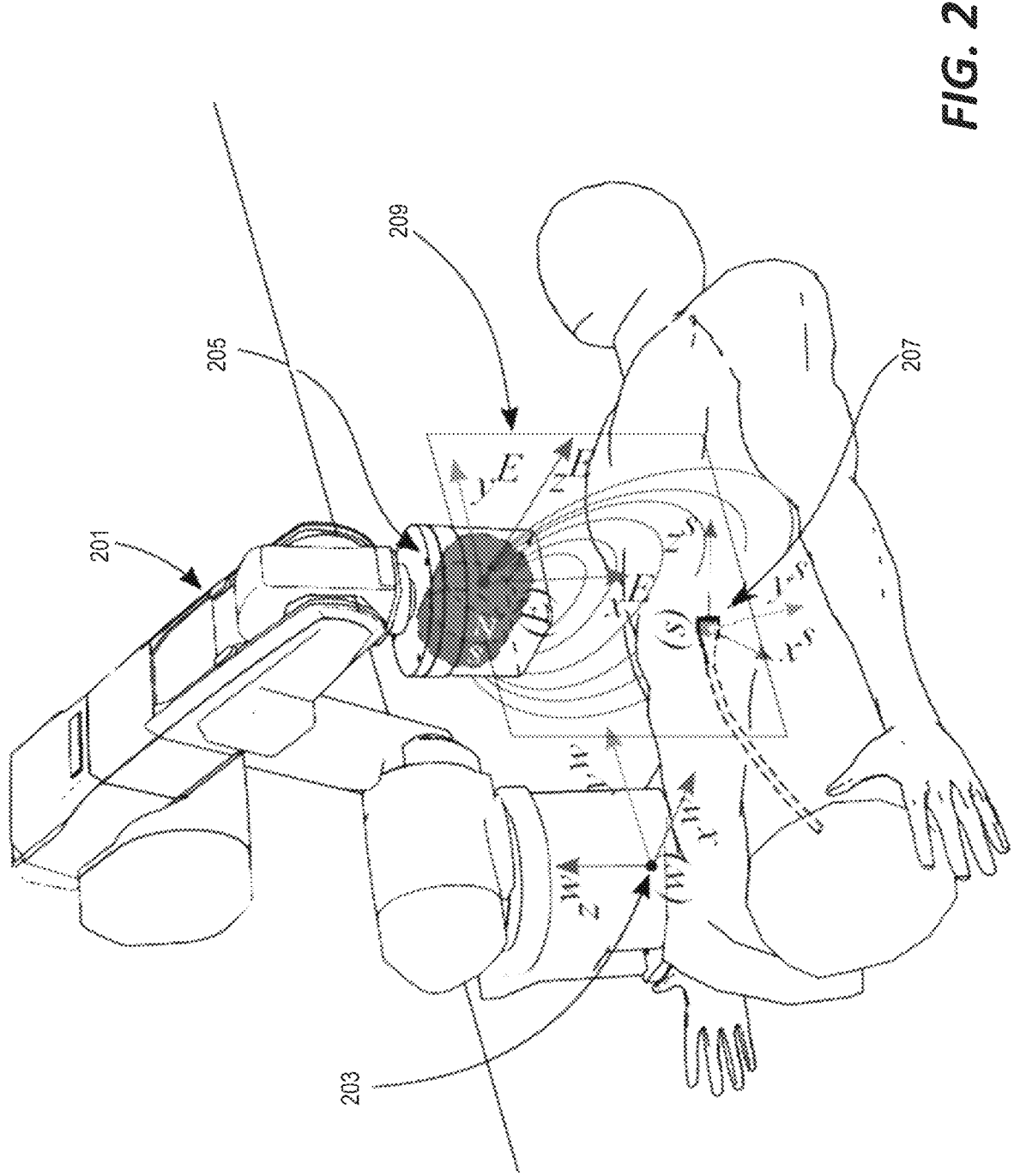
FIG. 2 is a perspective view of a robotic system for controlling movement and determining a localization of the capsule of FIG. 1.

As discussed above, the endoscope 100 of FIG. 1 includes a magnet embedded in the tip (i.e., in the capsule 101). This magnet is used to control the movement of the capsule 101 at the distal end of the endoscope body 103 as the endoscope moves through a cavity or channel to a target site. FIG. 2 illustrates an example of a system for controlling the movement of the capsule 101. The system includes a controllably articulatable robotic arm 201. The robotic arm 201 is mounted to a stationary base 203 and has an external permanent magnet (EPM) 205 affixed to a distal end of the robotic arm 201. Through the controlled movement of the robotic arm 201, the position and orientation of the EPM 205 is adjusted. Because the permanent magnet 207 of the capsule 101 is magnetically attracted to the EPM 205 at the distal end of the robotic arm 201, movement of the capsule 101 can be affected and regulated by controlled movement of the EPM 205 by the robotic arm 201.

Figure 4:
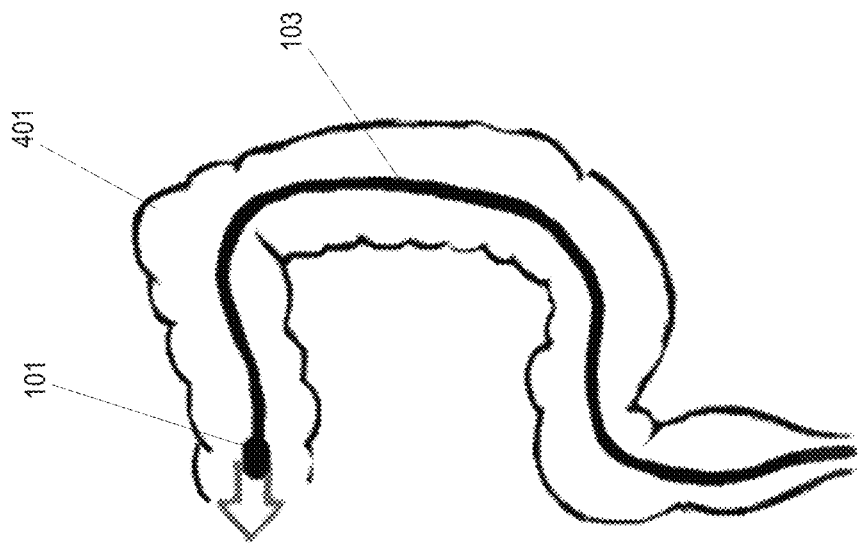
FIG. 4 is a schematic view of the flexible endoscope of FIG. 1 positioned in a human intestine.
Figure 3:
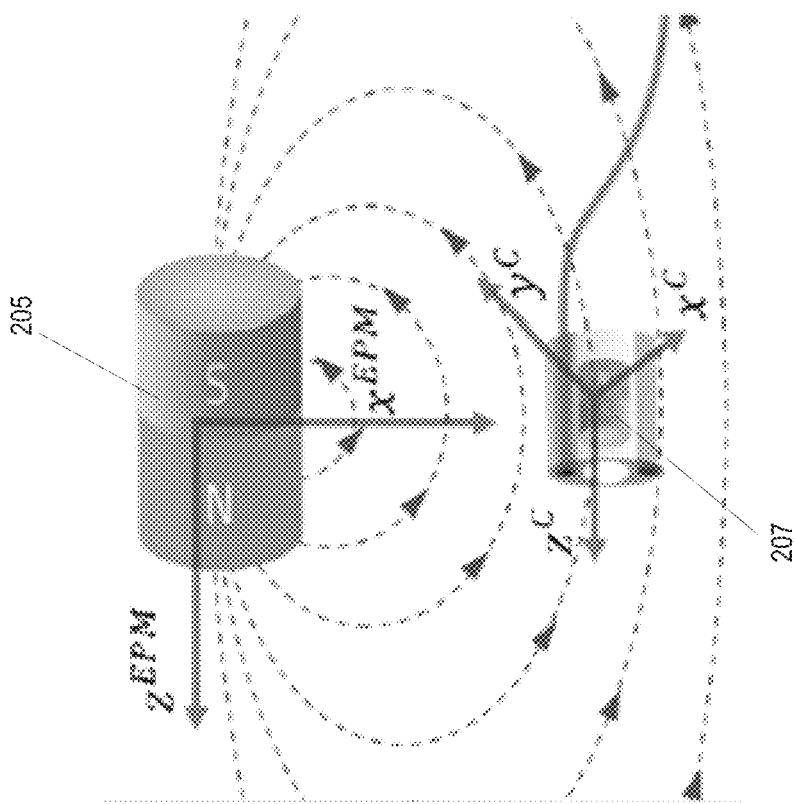
FIG. 3 is a schematic view of a magnetic field applied by a permanent magnet of the robotic system of FIG. 2 to the capsule of FIG. 1.

As discussed in the examples below, a set of ground coordinates is defined relative to the stationary base 203 of the robotic arm 201. A coordinate frame for the EPM 205 is defined relative to the current pose and location of the EPM 205, which is known based on the controlled position of the robotic arm 201. The capsule 101 also has its own local coordinate frame. However, because the capsule 101 is located inside a body cavity, the local coordinate frame of the capsule cannot be directly observed. Instead, the position and orientation of the capsule 101 (i.e., the local coordinate frame of the capsule relative to the local coordinate frame of the EPM 205) is determined by measuring, at the capsule 101, the magnetic field applied to the capsule 101 by the EPM 205. FIG. 3 illustrates an example of a magnetic field generated by the EPM 205 and shows the capsule 101 with the capsule permanent magnet 207 positioned within the magnetic field generated by the EPM 205. This magnetic field is used to both identify a current position/orientation of the capsule magnet 207 relative to the EPM 205 while also manipulating movement of the capsule. FIG. 4 shows an example of the capsule 101 and the endoscope body 103 positioned in a human intestine 401. As the EPM 205 is controllably moved by the robotic arm 201, the capsule 101 moves similarly due to the magnetic attraction. As the robotic arm is controlled to move the capsule 101 through the cavity 401, the compliant/flexible endoscope body 103 follows passively behind the capsule 101. In some implementations, the capsule 101 and robotic arm 201 can be configured such that movement of the EPM 205 controls an actuation of a tool of the capsule 101 (e.g., deploying a robotic device) in addition to or instead of adjusting the position of the capsule 101 itself.

Figure 5:
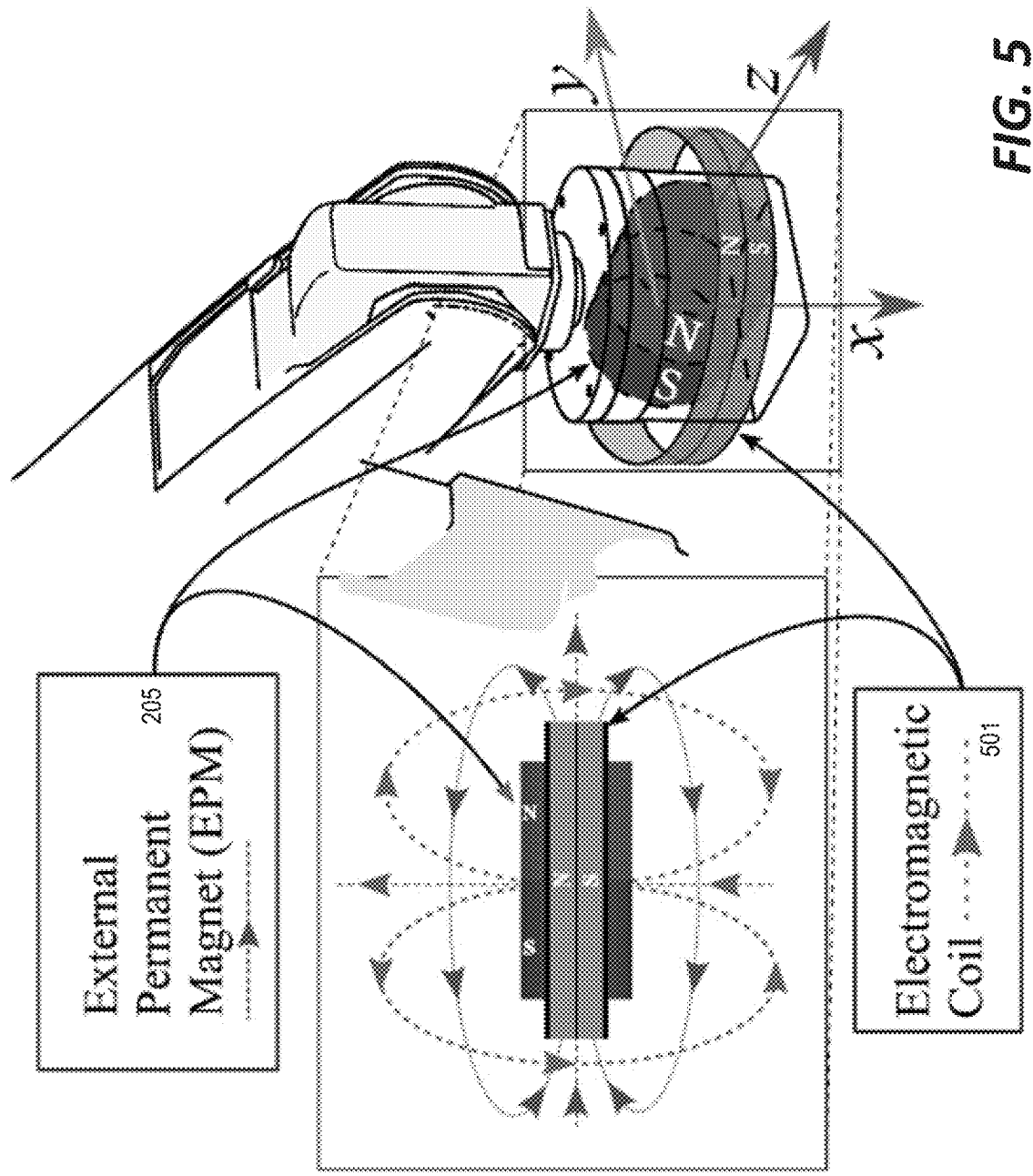
FIG. 5 is a perspective view of an electronic permanent magnet (EPM) and an orthogonally positioned electromagnetic coil coupled to a distal end of the robotic system of FIG. 2.

In many cases, the pose and location of the capsule 101 (e.g., localization) relative to the EPM 205 can be identified by a bijective mapping for all positions in a given workspace to magnetic field vectors (e.g., applied by the EPM 205) and changes in the magnetic field always occur for changes in position. However, this assumption fails to hold on a singularity plane 209 (illustrated in FIG. 2) of the EPM 205 defined as the plane normal to the dipole moment that passes through the center of the magnet 205. In other words, when the capsule 101 is in the xy-plane 209 of the EPM frame, the system loses one degree of freedom resulting in infinite solutions to the localization problem. To mitigate this problem, an additional source of magnetic field is added to the system. In the example of FIG. 5, an electromagnetic coil 501 is positioned around the EPM 205 as illustrated in FIG. 5 such that the magnetic moment of the electromagnetic coil 501 is orthogonal to the magnetic moment of the EPM 205. The magnetic field generated by the EPM 205 and the coil 501 permeates the workspace and, therefore, measurement of the two fields in conjunction with inertial measurements can be used to determine the pose of the capsule 101 in real-time.

The electromagnetic coil 501 is operated to generate a sinusoidal magnetic field that can be sensed by a plurality of magnetic field sensors positioned within the capsule 101. However, the magnetic field generated by the electromagnetic coil 501 does not adversely affect the capsule's actuation using the EPM 205. This is because (1) the signal strength of the coil 501 can be reduced owing to signal processing techniques that allow detection of small signals and (2) the high frequency with which the generated field oscillates is too high to excite the capsule 101.

Figure 6:
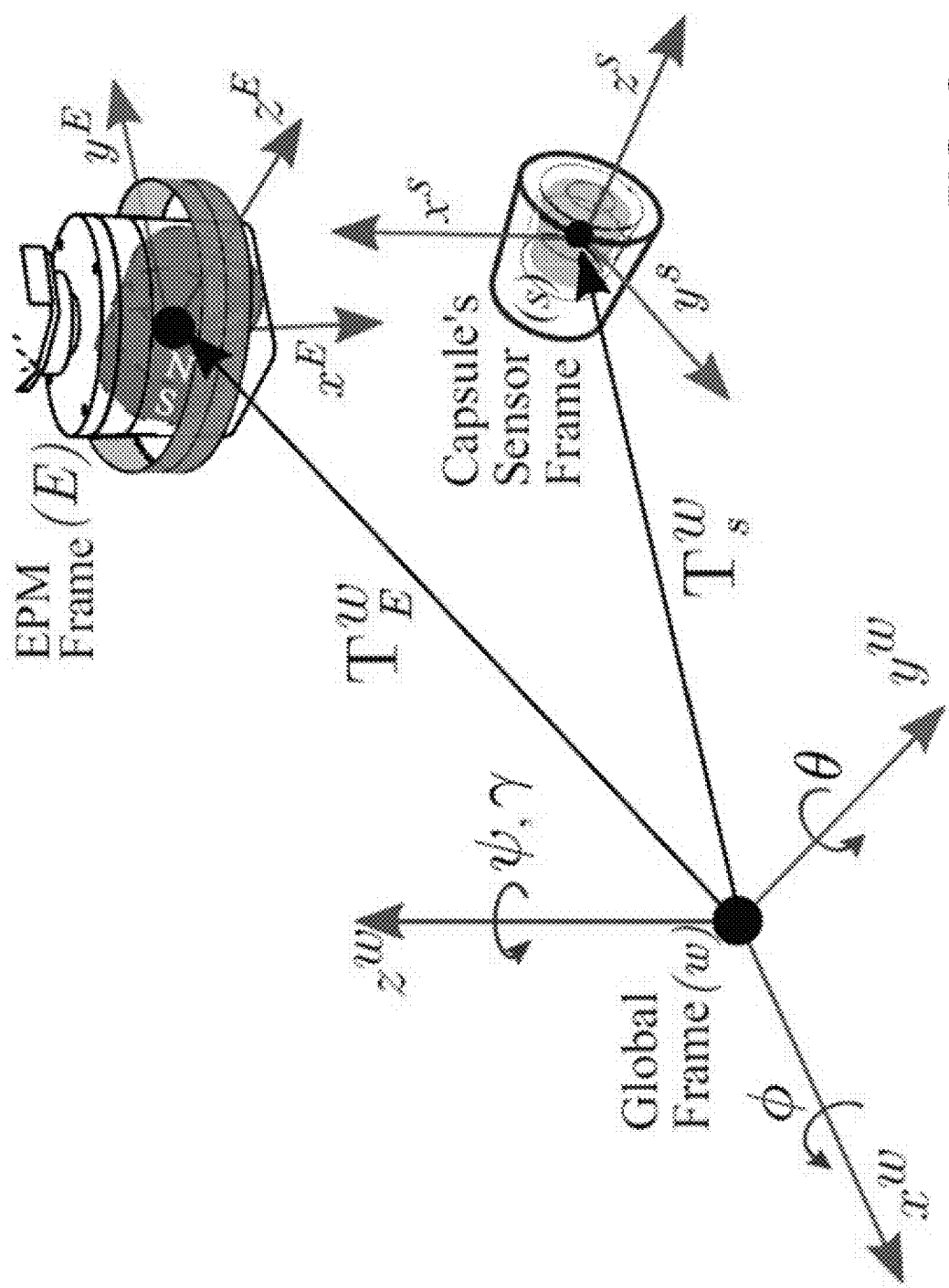
FIG. 6 is a schematic view of the local coordinate frames of the EPM of FIG. 5 and the capsule of FIG. 1 relative to a global coordinate frame.

FIG. 6 illustrates an example of the local coordinate frame of the EPM 205 (the "EPM Frame (E)") and the local coordinate frame of the capsule 101 (e.g., the "Capsule's Sensor Frame (s)") as well as the global coordinate frame ("Global Frame (w)"). The three-dimensional coordinates of the EPM Frame ($x^E$, $y^E$, $z^E$) can be defined relative to the three-dimensional coordinates of the global frame ($x^w$, $y^w$, $z^w$) by defining a homogeneous transformation $T_E^w$, for example, based on a known position of the EPM 205 determined by the controlled pose of the robotic arm 201. A homogeneous transform $T_s^w$ between the three-dimensional coordinates of the Capsule's Sensor Frame ($x^s$, $y^s$, $z^s$) and the three-dimensional coordinates of the global frame ($x^w$, $y^w$, $z^w$) as well as the yaw $\psi$, roll $\phi$, and pitch $\theta$ of the capsule can be determined based on the magnetic field that is induced by the EPM 205 and the coil 501 and that is detected by the magnetic field sensors of the capsule 101.

Figure 7:
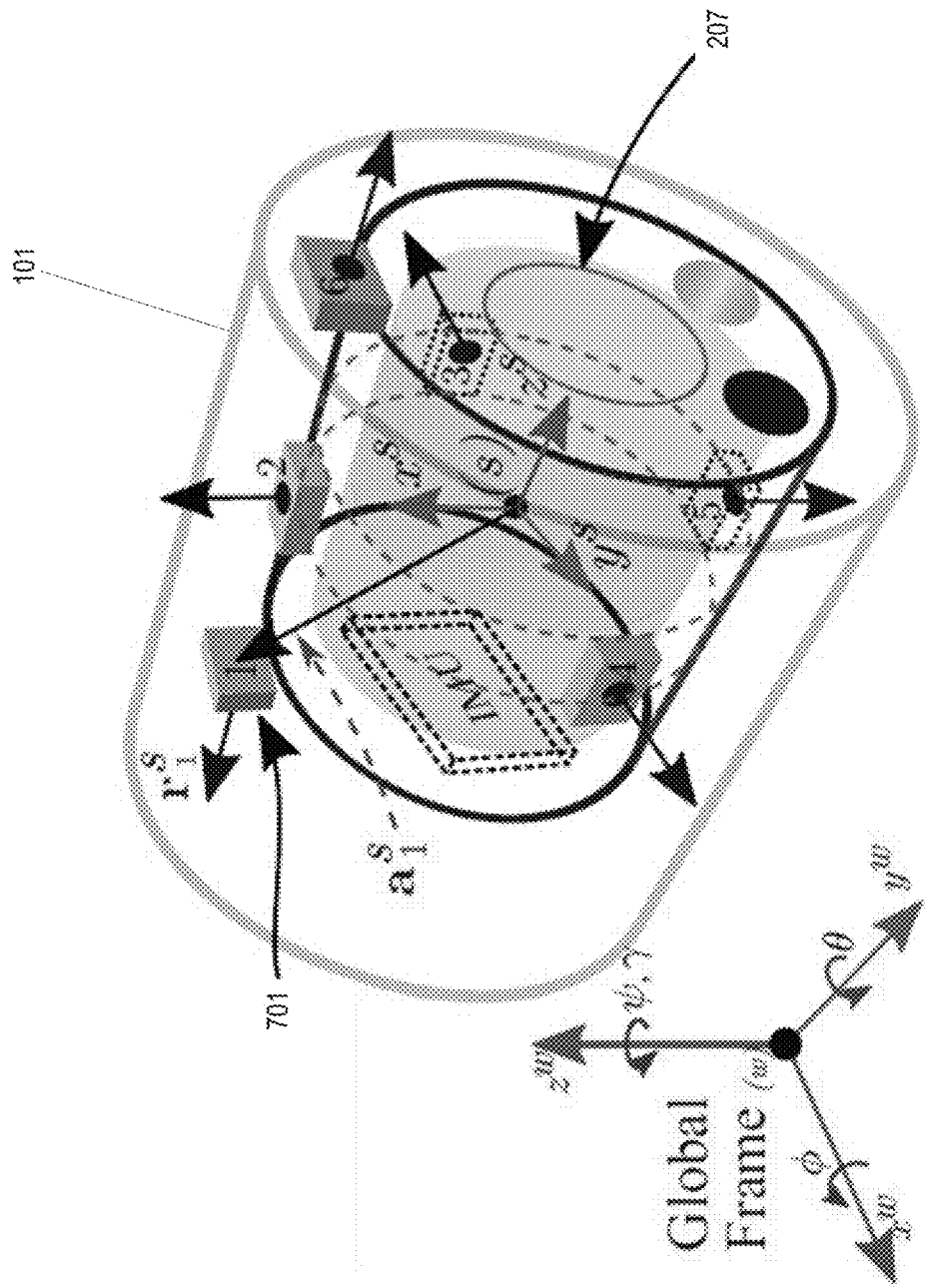
FIG. 7 is a partially transparent perspective view of the capsule of FIG. 1.

FIG. 7 illustrates a partially transparent view of the capsule 101. The permanent magnetic 207 is positioned within the housing of the capsule 101 (as described in further detail below) and a plurality of Hall Effect sensors 701 are affixed to the capsule 101 at locations around the capsule 101. In the example of FIG. 7, four Hall Effect sensors (labeled 2, 3, 4, and 5) are positioned around the circumference of the internal permanent magnet 207. Two more Hall Effect sensors (labeled 1 and 6) are positioned at the front and rear of the capsule 101.

Figure 8:
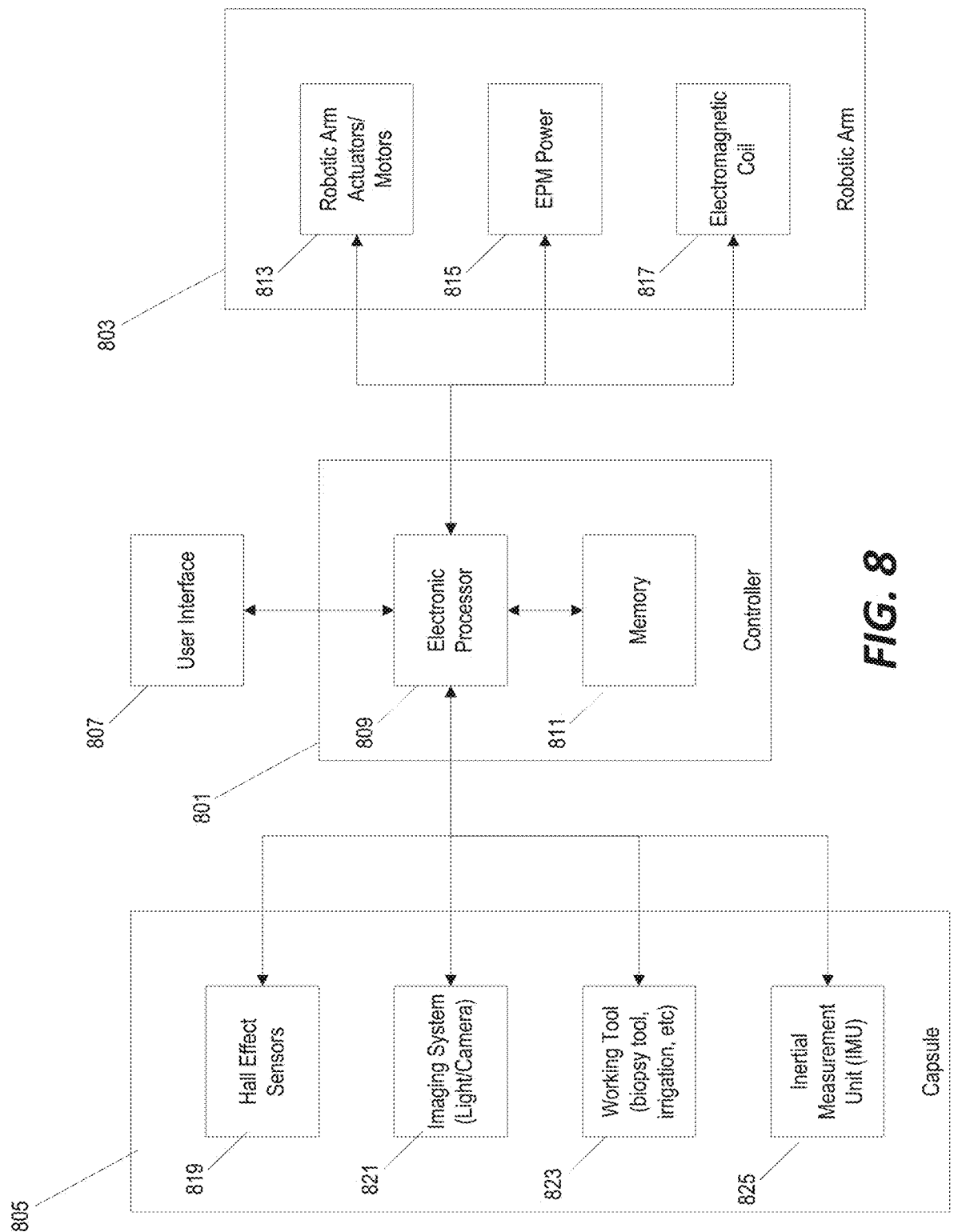
FIG. 8 is a block diagram of a control system for the capsule of FIG. 1 and the robotic system of FIG. 2.

FIG. 8 shows an example of a control system for operating the capsule 101 and robotic arm 201 as illustrated in the examples above. A controller 801 is communicatively coupled to the robotic arm 803, the capsule 805, and a user interface 807. In various different implementations, the user interface 807 may include, for example, a joystick-type controller, a screen, and/or a graphical user interface. In some cases, the user interface displays a location and pose of the capsule 101 relative to the cavity to allow the user to control movement of the capsule 101. In some cases, the user interface is configured to display the output of the capsule camera while the user operates other tools of the capsule 101 (e.g., the biopsy tool 111 of FIG. 1).

The controller 801 includes an electronic processor 809 and a non-transitory computer-readable memory 811. The memory 811 stores instructions that are executed by the electronic processor 809 to provide the functionality of the controller 801 such as described herein. The control 801 generates and transmits control signals to the robotic arm actuators/motors 813 (e.g., to control the movement of the robotic arm), to a power source/circuit 815 for the EPM 205 (e.g., to apply power to the EPM 205), and to the electromagnetic coil 817 (e.g., the cause the electromagnetic coil to generate the sinusoidal magnetic field). The system may be configured to provide these (and potentially other) control signals to the various component of the robotic arm 803 through wired and/or wireless connections. Similarly, through a wired connection that runs to the capsule 101 through the endoscope body 103, the controller 801 receives measurement data from the Hall Effect sensors 819 and an inertial measurement unit (IMU) 825 of the capsule. In some implementations, the controller 801 may also be configured to provide control signals to an imaging system 821 (e.g., including the light source 113 and the camera 109) and to receive image data captured by the imaging system 821. Similarly, in some implementations, the controller 801 may be configured to provide control signals to a working tool 823 (e.g., an electronically controlled biopsy tool and/or a pump for an irrigation/insufflation system).

In the example of FIG. 8, a single controller 801 is illustrated as communicating with and controlling both the capsule 805 and the robotic arm 803. However, in some implementations, the system may include multiple different controllers. For example, instead of a central controller 801, separate controllers may be included in the robotic arm 803, the capsule 805, and the User Interface 807.

Figure 9:
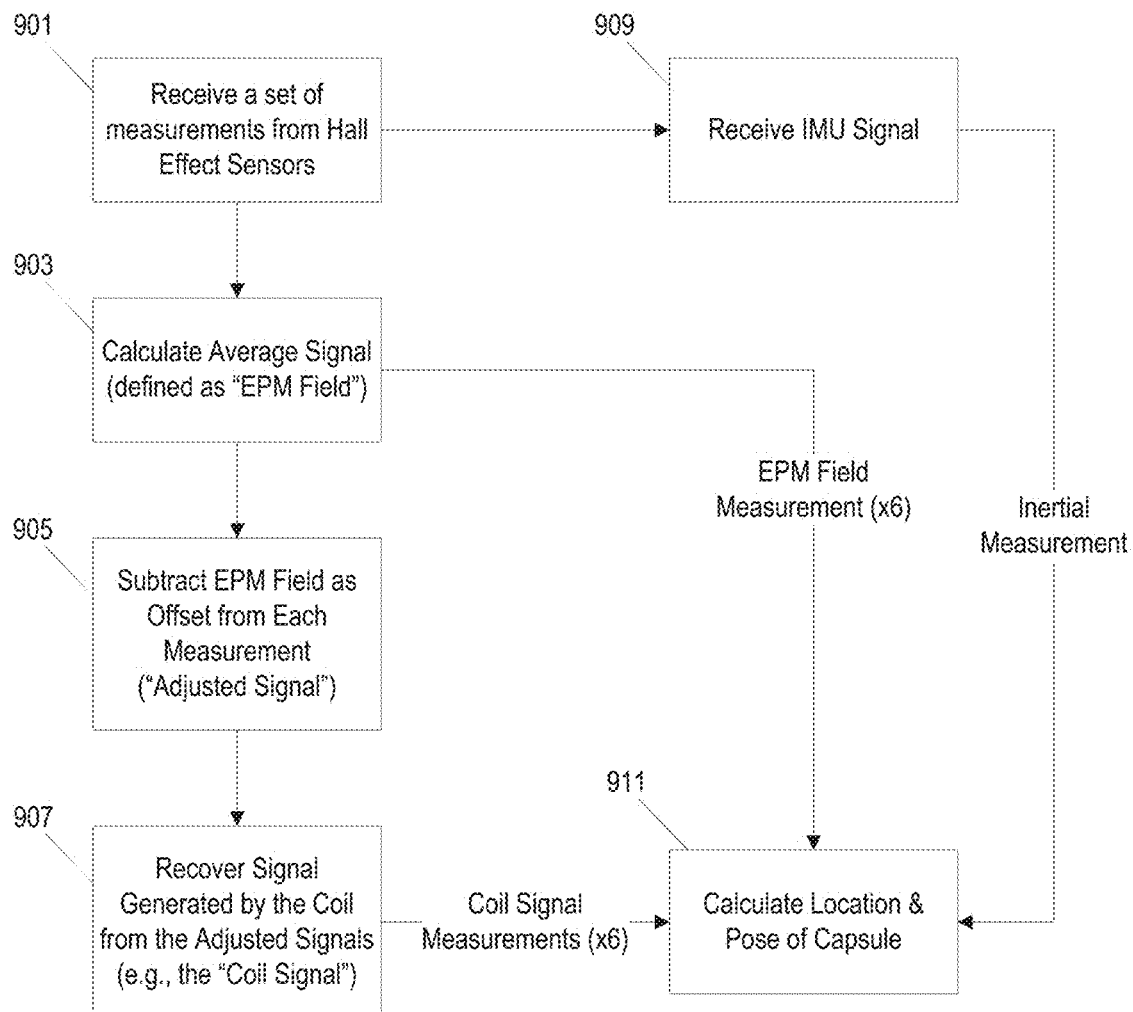
FIG. 9 is a flowchart of a method for determining a localization of the capsule of FIG. 1 using the robotic system of FIG. 2 and the electromagnetic coil/EPM of FIG. 5.

FIG. 9 illustrates a method executed by the controller 801 for localization of the capsule 101 (i.e., determining a pose and location of the capsule 101 relative to a global coordinate frame). As shown in FIG. 7, two Hall-Effect sensor triplets (e.g., a total of 6 Hall Effect sensors) are positioned around the internal magnet of the capsule 101 so as to measure only the magnetic fields generated by external magnetic field sources (e.g., sources outside of the capsule 101). In this configuration, the magnetic field generated by the internal magnet is small and constant and, therefore, can be treated as an offset in software. To distinguish between the magnetic field generated by the EPM 205 and the magnetic field generated by the electromagnetic coil 501, amplitude modulation is used with the Heterodyne principle. Because this method focuses on amplitude modulation, the signal generated by the electromagnetic coil can be thought of as a virtual DC signal modulated at a carrier frequency. In some implementations, the signal is demodulated at the capsule to recover the original virtual DC signal from the electromagnetic coil. The field from the EPM 205 is a DC offset on the received sinusoid and can be determined by calculating an average of the sensed signal.

As illustrated in FIG. 9, the controller 801 receives a set of measurements from the Hall Effect sensors of the capsule (step 901). In this particular example, the set of measurements includes the measured output of each of the six Hall Effect sensors over a duration of 10 ms and are collected at a defined sample rate. However, the duration and sample rate can be adjusted/tuned for other specific uses and implementations. The average of the collected samples is calculated for each of the six Hall Effect sensors (step 903). The calculated average of the measurements from a particular Hall Effect sensor is indicative of the magnetic field generated by the EPM 205 and sensed by that particular Hall Effect sensor. As discussed above, component of the sensed magnetic field generated by the electromagnetic coil is isolated by subtracting the EPM field value for a particular Hall Effect sensor from each collected measurement for that particular Hall Effect sensor as a "DC offset" in order to generate an "adjusted signal" (step 905). The adjusted signal is then multiplied with locally generated sine and cosine signals (according to the Heterodyne principle) and averaged (using a low pass filter) to recover the portion of the total magnetic field sensed by a particular Hall Effect sensor that was generated by the electromagnetic coil (step 907).

Steps 903, 905, and 907 in FIG. 9 are repeated for each of the six different Hall Effect Sensors resulting in a calculated EPM Field measurement and a calculated Coil Signal Measurement for each of the six individual Hall Effect sensors. The controller 101 also receives a inertial measurement output from the capsule IMU (step 909) and calculates a location and pose of the capsule 101 based on the inertial measurement, the EPM field measurement for each of the six Hall Effect sensors, and the Coil Signal Measurement for each of the six Hall Effect sensors (step 911).

In some implementations, the orientation of the capsule 101 is determined using data from the IMU using an explicit commentary filter. In other implementations, the controller 801 may be configured to utilize other methods for localization in addition to or instead of the explicit commentary filter. In one example, the controller 801 is configured to utilize a map search method where the two sets of magnetic field measurements are treated as two independent magnets. A magnetic field map is generated offline for both magnets and issued as a first and second lookup table. At each iteration of the algorithm, the EPM measurements will be used first to determine a localization of the capsule 101 using the first look up table. If the pose of the capsule 101 cannot be determined based on the EPM measurements because the capsule 101 is in the singularity plane 209 of the EPM 205, then the Coil Signal measurements will be used to determine the localization of the capsule 101 from the second look up table. Because the EPM 205 and the electromagnetic coil 501 are orthogonal to each other, the capsule 101 cannot be in a singularity for both magnets at the same time. Accordingly, the Coil Signal measurements and the second look up table can be used to disambiguate from the infinite solutions available when the capsule 101 is in the singularity plane 209 for the EPM 205.

In another example, the controller 801 is configured to determine a localization solution (e.g., an estimated pose and location of the capsule 101) using a particle filter. Particle filters are a type of Bayesian filters used for parameter estimation. A set of particles is randomly initialized in a workspace as proposals for the possible position of the capsule. In addition, to limit problems associated with gyro drift, the particles contain proposals for yaw error. At each iteration, the position of each particle is used to calculated the proposed magnetic field from the EPM 205 and the coil 501 at the location. The proposed field is then compared against the measured data and the particles that have proposed fields significantly different from the measured data are removed from the set of particles. At determined intervals, a new set of particles will be added to the existing set.

FIGS. 10A, 10B, 10C, and 10D illustrate one example of the components and assembly of a capsule such as capsule 101 described in the examples above. FIGS. 11A, 11B, 11C, and 11D illustrate an example of how the capsule of FIGS. 10A through 10D is coupled to a tip of an endoscope.

Figure 10A:
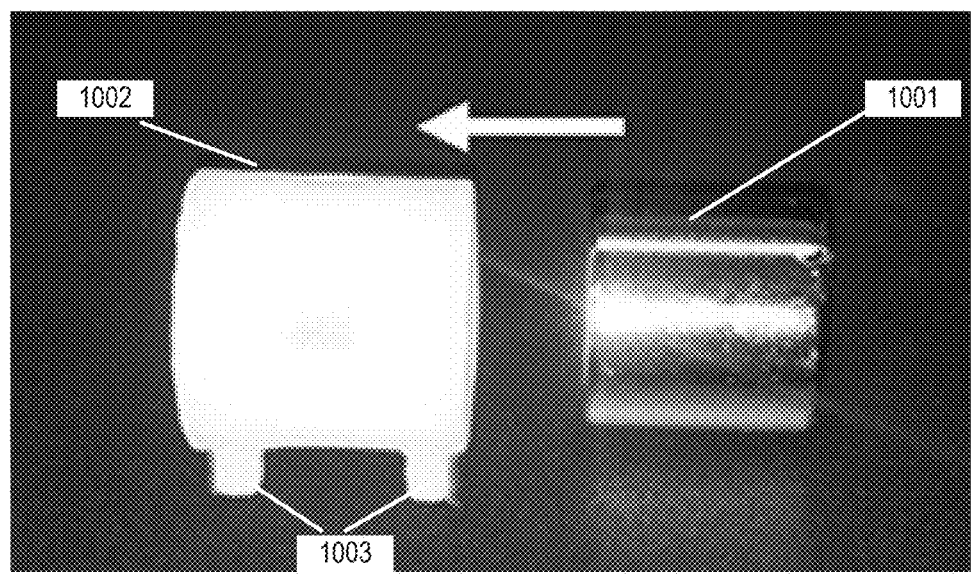
FIG. 10A is an elevation view of a magnet housing of the capsule of FIG. 1.

As shown in FIG. 10A, a small permanent magnet 1001 ($7/16"\times7/16"$) is slid into a magnet-housing 1002. The north pole of the magnet 1001 remains exposed. The magnet housing 1002 includes a pair of protrusions 1003 as discussed in further detail below. FIG. 10B illustrates a first side of a flexible circuit 1004. The flexible circuit 1004 includes a rectangular central strip and a pair of circular areas on either side of the central strip. A series of four Hall Effect sensors 1005, 1007, 1009, and 1011 are mounted to the flexible circuit 1004 along a central strip. Two additional Hall Effect sensors 1013, 1015 are each mounted on a different one of the circular areas opposite the central strip. An analog-to-digital converter 1017 is also affixed to one of the circular areas. FIG. 10C illustrates the opposite surface of the flexible circuit 1004. On the first circular area (on the opposite surface of the same circular area where the analog-to-digital converter 1017 is mounted), the inertial measurement unit (IMU) 1021 and a voltage regulator 1023 are affixed to the flexible circuit 1004. A bundle of wires 1019 also extends from this side of the first circular area. An LED 1025 is mounted to the flexible circuit 1004 on the other circular area.

Figure 10D:
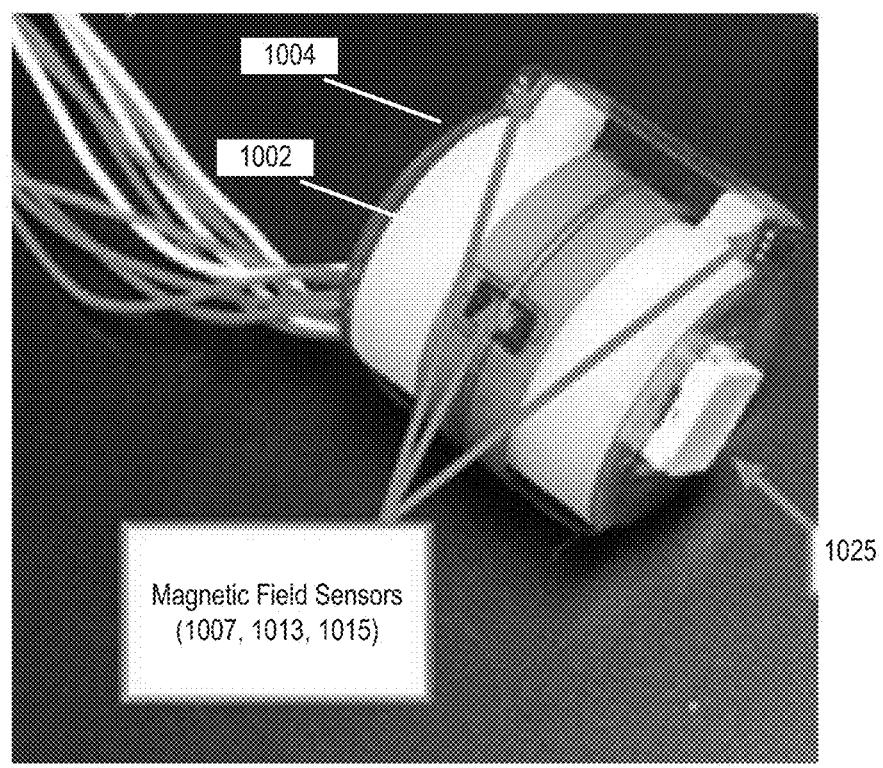
FIG. 10D is a perspective view of the assembled magnetic housing of FIG. 10A coupled to the flexible circuit of FIG. 10B.
Figure 10B:
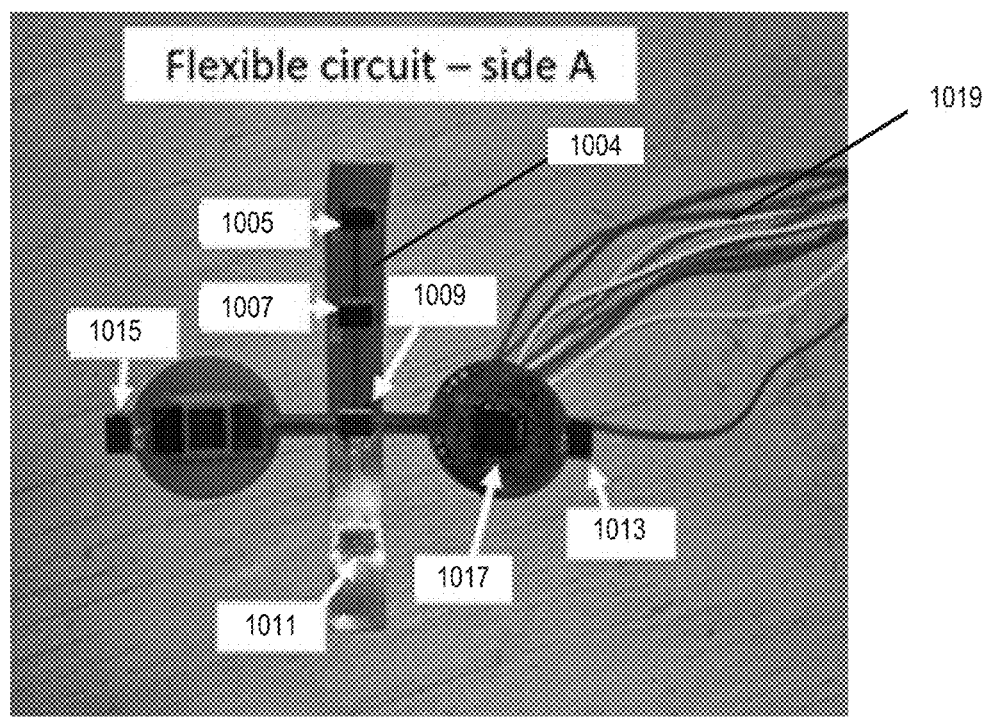
FIG. 10B is an overhead view of a first side of a flexible circuit of the capsule of FIG. 1.
Figure 10C:
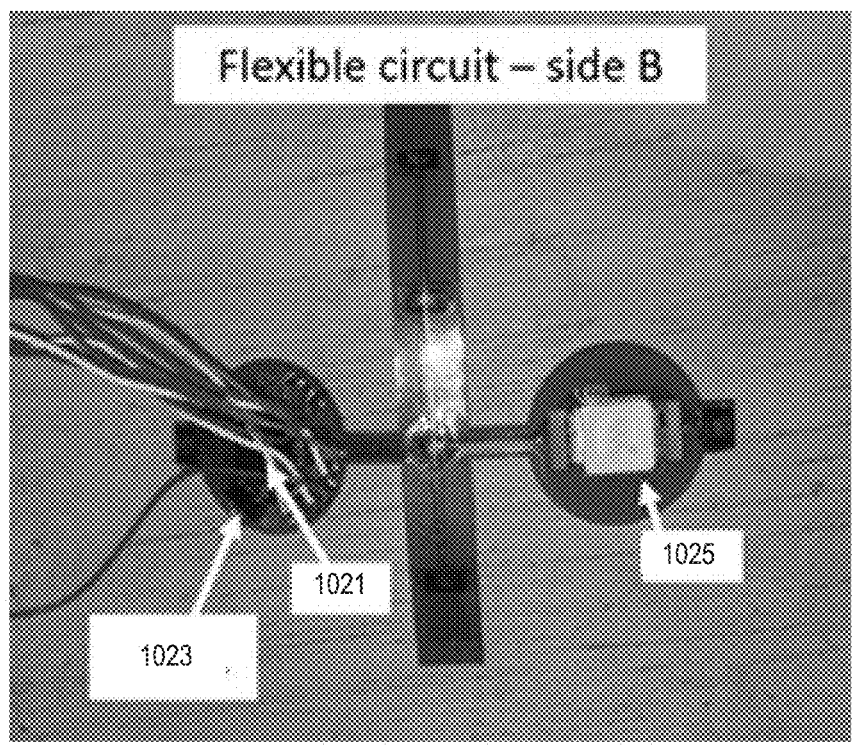
FIG. 10C is an overhead view of a second side of the flexible circuit of FIG. 10B.

As shown in FIG. 10D, the flexible circuit 1004 is wrapped around the exterior of the magnet housing 1002 so that each circular area of the flexible surface is positioned over a different end of the cylindrical magnet housing 1002 and so that the Hall Effect sensors 1013, 1015 are aligned with the protrusions 1003. The central strip of the flexible circuit 1004 is wrapped around an exterior of the magnet housing 1002 so that the other four Hall Effect sensors are positioned at equal distances around the circumference. In the perspective view of FIG. 10D, the LED 1025 is visible on the front end of the magnet housing 1002, the bundle of wires 1019 is visible extending from a rear end of the magnet housing 1002, and the positioning of three of the six Hall Effect sensors (1007, 1013, 1015) can be seen. The placement of the other Hall Effect sensors is illustrated above in FIG. 7. In the example of FIG. 10D, the LED 1025 is positioned on the exposed side of the magnet with the thickness of the LED 1025 directed away from the magnet 1001.

Figure 11B:
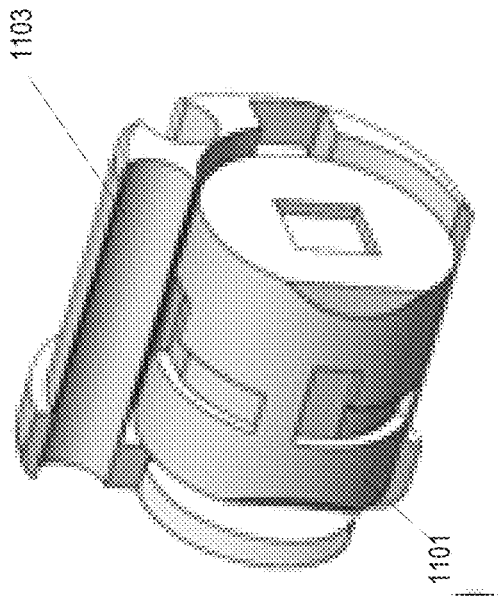
FIG. 11B is a perspective view of the magnetic housing assembly of FIG. 10D coupled to a first half of the exterior capsule shell.
Figure 11D:
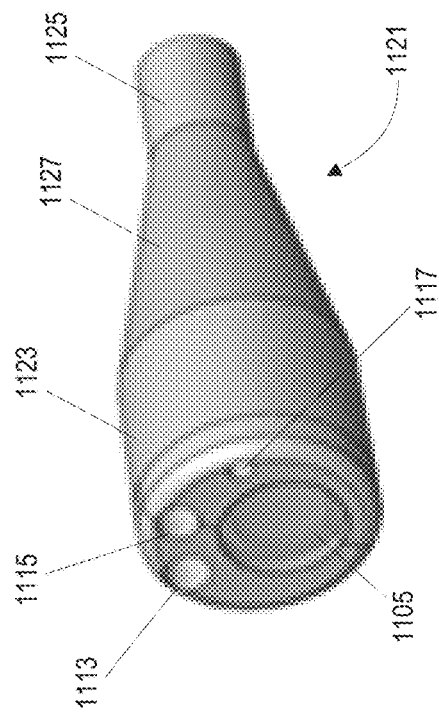
FIG. 11D is a perspective view of the capsule of FIG. 11C partially encased in a flexible outer sleeve.
Figure 11A:
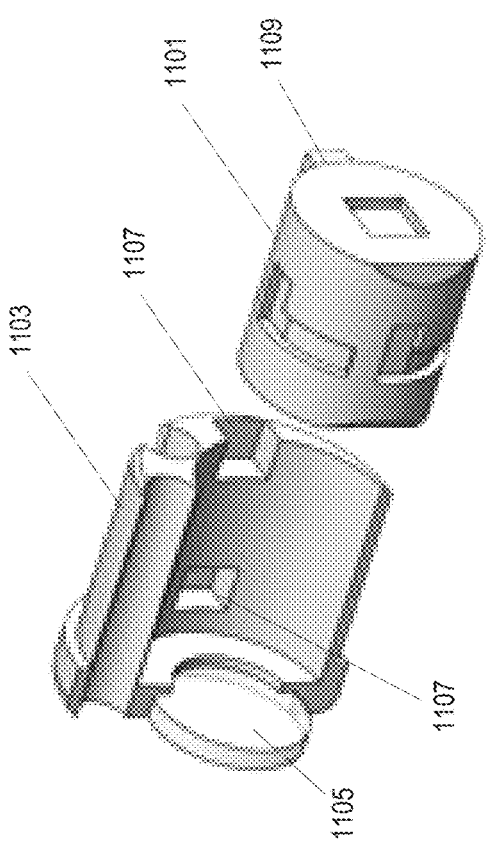
FIG. 11A is an exploded perspective view of the magnetic housing assembly of FIG. 10D is an exterior capsule shell.

After the flexible circuit 1004 is wrapped around the magnet housing 1002 as shown in FIG. 10D, the magnet housing 1001 is positioned within an exterior shell. FIG. 11A shows the assembled magnet housing 1101 and a first half of the exterior shell 1103. A lens 1105 for the light source is coupled to the first half of the exterior shell 1103.

The first half of the exterior shell is molded to include a pair of key slots 1107 that engage the protrusions 1109 of the magnet housing 1101 to prevent relative motion inside the capsule. After the magnet housing 1101 is positioned in the first half of the exterior shell 1103 with its protrusions 1109 engaging the key slots 1107, as shown in FIG. 11B, a second half of the exterior shell 1111 is coupled to the first half of the exterior shell 1103 to surround the magnet housing 1101 as shown in FIG. 11C.

Figure 11C:
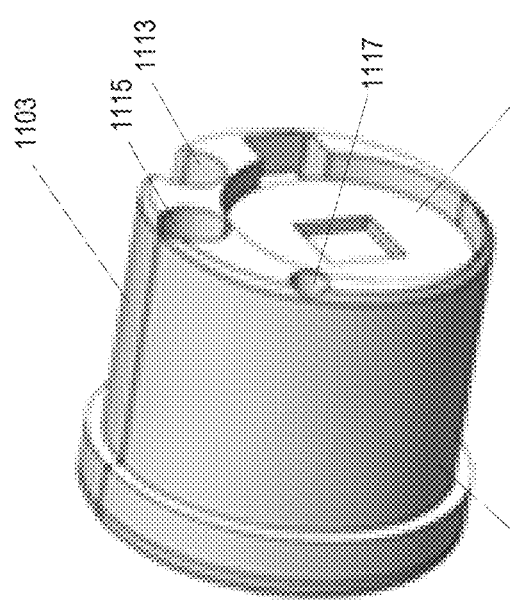
FIG. 11C is a perspective view of the magnetic housing assembly of FIG. 10D circumferentially enclosed by an exterior capsule shell.

As also shown in FIG. 11C, the two halves of the assembled exterior shell (1103, 1111) are molded to provide a series of channels through the capsule along the length of the magnet housing 1101. In the example of FIG. 11C, the exterior shell provides three separate channels through the capsule: a biopsy tool channel 1113, a camera channel 1115, and an irrigation/insufflation channel 1117. FIG. 11D shows the front side of the capsule (e.g., the distal end of the endoscope). In FIG. 11D, the lens 1105 for the light source is visible as well as the terminal ends of the biopsy tool channel 1113, the camera channel 1115, and the irrigation/insufflation channel 1117.

As shown in FIG. 11D, a flexible sleeve 1121 is positioned around the assembled capsule covering at least a part of the exterior surface of the capsule. As discussed above, the flexible sleeve 1121 is configured to fits tightly around the circumference of the capsule and the circumference of the endoscope body to provide a flexible coupling between the capsule and the endoscope body. In the example of FIG. 11D, the flexible sleeve 1121 includes a first tubular portion 1123 sized to fit snuggly around the exterior shell of the capsule and a second tubular portion 1125 sized to fit snuggly around the exterior of the endoscope body (as illustrated in FIG. 1). The flexible sleeve 1121 also includes a tapered portion 1127 in which the diameter of the flexible sleeve is gradually reduced from the capsule size (tubular portion 1123) to the endoscope body size (tubular portion 1125).

Thus, the invention provides, among other things, systems and methods for controlling a movement or actuation of a capsule device and for determining a position and orientation of the capsule device. Various features and advantages of the invention are set forth in the following claims.

What is claimed is:

1. A system for controlling and monitoring movement of a capsule, the system comprising:
    a controllable robotic arm;
    an external permanent magnet coupled to a distal end of the controllable robotic arm;
    an electromagnetic coil positioned around the external permanent magnet with a magnetic moment of the electromagnetic coil positioned orthogonal to a magnetic moment of the external permanent magnet;
    a capsule including a plurality of magnetic field sensors positioned at different locations on the capsule and an internal permanent magnet positioned inside the capsule; and
    a controller configured to
        adjust a position of the capsule by controllably adjusting a position of the external permanent magnet by movement of the robotic arm, wherein movement of the external permanent magnet causes movement of the capsule due to magnetic attraction between the external permanent magnet and the internal permanent magnet,
        operate the electromagnetic coil to generate a sinusoidal magnetic field,
        periodically receive signals indicative of magnetic field vectors sensed by each of the magnetic field sensors of the capsule,
        calculate an average signal measurement for a first one of the plurality of magnetic field sensors,
        determine a magnetic field vector measurement for the first one of the plurality of magnetic field sensors,
        determine a magnetic field signal applied by the electromagnetic coil to the first one of the plurality of magnetic field sensors based at least in part on a difference between the magnetic field vector measurement of a sequence of magnetic field vector measurements received from the first one of the plurality of magnetic field sensors and the average signal measurement for the first one of the plurality of magnetic field sensors, and
        determine a pose of the capsule based at least in part on the determined magnetic field signal applied by the electromagnetic coil to the first one of the plurality of magnetic field sensors.

2. The system of claim 1, wherein the controller is configured to determine the pose of the capsule based at least in part on a combination of determined magnetic field signals applied by the electromagnetic coil to each magnetic field sensor of the plurality of magnetic field sensors.

3. The system of claim 1, wherein the controller is further configured to determine a magnetic field signal applied by the external permanent magnet to the first one of the plurality of magnetic field sensors as being equal to the average signal measurement calculated for the first one of the plurality of magnetic field sensors.

4. The system of claim 3, wherein the controller is configured to determine the pose of the capsule based at least in part on a combination of determined magnetic field signals applied by the electromagnetic coil to each magnetic field sensor of the plurality of magnetic field sensors and a combination of determined magnetic field signals applied by the external permanent magnet to each magnetic field sensor of the plurality of magnetic field sensors.

5. The system of claim 1, further comprising:
    a flexible endoscope body coupled to a proximal end of the capsule; and
    a flexible sleeve configured to fit snuggly around at least a part of an external surface of the capsule and to fit snuggly around at least a part of an external surface of the flexible endoscope body to provide a flexible and compliant coupling between the capsule and the endoscope body.

6. The system of claim 5, wherein the capsule is cylindrical and has a first diameter, wherein the flexible endoscope body is tubular and has a second diameter, the second diameter being smaller than the first diameter, and wherein the flexible sleeve includes
    a first tubular portion sized to fit snuggly around the first diameter,
    a second tubular portion sized to fit snuggly around the second diameter, and
    a tapered portion coupling the first tubular portion to the second tubular portion and configured to gradually reduce the diameter of the flexible sleeve from the first diameter of the first tubular portion to the second diameter of the second tubular portion.

* * * * *